(12) United States Patent
Masuda

(10) Patent No.: US 11,213,444 B2
(45) Date of Patent: Jan. 4, 2022

(54) ON-BED STATE MONITORING SYSTEM

(71) Applicant: Minebea Mitsumi Inc., Nagano (JP)

(72) Inventor: Shigemi Masuda, Fukuroi (JP)

(73) Assignee: MINEBEA MITSUMI INC., Nagano (JP)

( * ) Notice: Subject to any disclaimer, the term of this patent is extended or adjusted under 35 U.S.C. 154(b) by 0 days.

(21) Appl. No.: 16/633,961

(22) PCT Filed: Jul. 26, 2018

(86) PCT No.: PCT/JP2018/028046
§ 371 (c)(1),
(2) Date: Jan. 24, 2020

(87) PCT Pub. No.: WO2019/022186
PCT Pub. Date: Jan. 31, 2019

(65) Prior Publication Data
US 2020/0155392 A1 May 21, 2020

(30) Foreign Application Priority Data
Jul. 27, 2017 (JP) .............................. JP2017-145040

(51) Int. Cl.
*G08B 23/00* (2006.01)
*A61G 7/05* (2006.01)
(Continued)

(52) U.S. Cl.
CPC ............... *A61G 7/05* (2013.01); *G08B 21/02* (2013.01); *G16H 40/63* (2018.01); *A61G 2203/32* (2013.01)

(58) Field of Classification Search
CPC ...... A61G 2203/32; A61G 7/05; G08B 21/02; G08B 25/04; G16H 40/63
(Continued)

(56) References Cited

U.S. PATENT DOCUMENTS 8,279,057 B2 10/2012 Hirose
9,795,321 B2 10/2017 Shimizu
(Continued)

FOREIGN PATENT DOCUMENTS

CN 101313877 A 12/2008
JP 11-290394 A 10/1999
(Continued)

OTHER PUBLICATIONS

English translation of Written Opinion for corresponding International Application No. PCT/JP2018/028046 dated Sep. 18, 2018.
(Continued)

*Primary Examiner* — Naomi J Small
(74) *Attorney, Agent, or Firm* — Pearne & Gordon LLP

(57) ABSTRACT

An in-bed state monitoring system (100) for monitoring an in-bed state of a subject on a bed includes: four load detectors (11, 12, 13, 14) which are configured to be placed at four corners of the bed to detect a load of the subject; and an edge sitting posture determining unit (33) configured to predict that the subject is reaching a state of edge sitting posture based on a change in a magnitude relation between detection values from two load detectors, which are of the four load detectors and are placed to interpose the bed between the two load detectors in a diagonal direction of the bed.

9 Claims, 10 Drawing Sheets

(51) Int. Cl.
*G16H 40/63* (2018.01)
*G08B 21/02* (2006.01)
(58) Field of Classification Search
USPC .................................................. 340/573.7
See application file for complete search history.

(56) References Cited

U.S. PATENT DOCUMENTS

| | | | |
|---|---|---|---|
| 2008/0132808 A1 | 6/2008 | Lokhorst et al. | |
| 2008/0217074 A1 | 9/2008 | Kokaka et al. | |
| 2009/0260158 A1* | 10/2009 | Kazuno | G01G 19/445 5/600 |
| 2010/0231376 A1 | 9/2010 | Hirose | |
| 2013/0205501 A1* | 8/2013 | Robertson | A61G 7/018 5/611 |
| 2015/0221202 A1* | 8/2015 | Russell | A61B 5/1117 340/573.7 |
| 2016/0007886 A1* | 1/2016 | Shimizu | G08B 29/185 340/573.1 |
| 2016/0007887 A1* | 1/2016 | Shimizu | G01L 1/205 340/573.4 |
| 2016/0220114 A1 | 8/2016 | Norita | |

FOREIGN PATENT DOCUMENTS

| | | |
|---|---|---|
| JP | 4002905 B2 | 11/2007 |
| JP | 2007-330659 A | 12/2007 |
| JP | 2008-206869 A | 9/2008 |
| JP | 2008-216155 A | 9/2008 |
| JP | 4676924 B2 | 4/2011 |
| JP | 2011-130827 A | 7/2011 |
| JP | 4829020 B2 | 11/2011 |
| JP | 4965904 B2 | 7/2012 |
| JP | 5086996 B2 | 11/2012 |
| JP | 2012-250046 A | 12/2012 |
| JP | 2015-008920 A | 1/2015 |
| WO | 2016/152424 A1 | 9/2016 |

OTHER PUBLICATIONS

International Search Report for corresponding International Application No. PCT/JP2018/028046 dated Sep. 18, 2018.
Written Opinion for corresponding International Application No. PCT/JP2018/028046 dated Sep. 18, 2018.
Decision to Grant a Patent dated Nov. 6, 2018 for corresponding Japanese Application No. 2017-145040 and English translation.
Extended European Search Report dated Jan. 12, 2021 for corresponding European Application No. 18837425.0.
Office Action dated Jan. 22, 2021 for corresponding Chinese Application No. 201880047206.6 and English translation.
Office Action dated Oct. 21, 2021 for corresponding Chinese Application No. 201880047206.6 and English translation.

* cited by examiner

Fig. 5
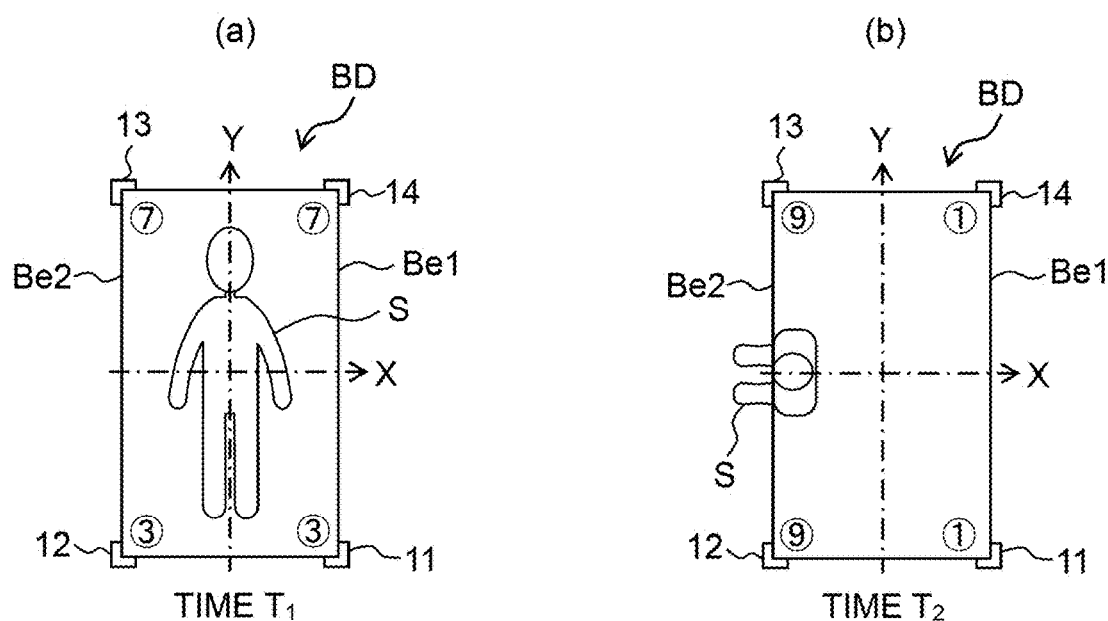
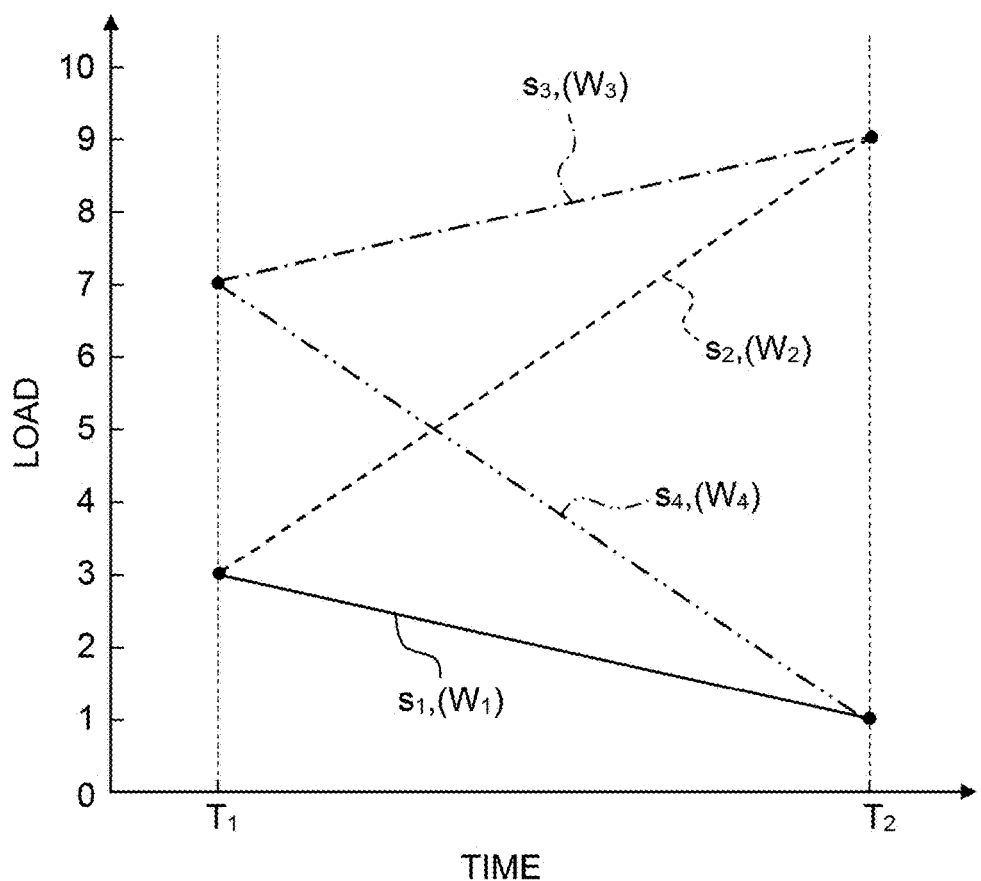

Fig. 6
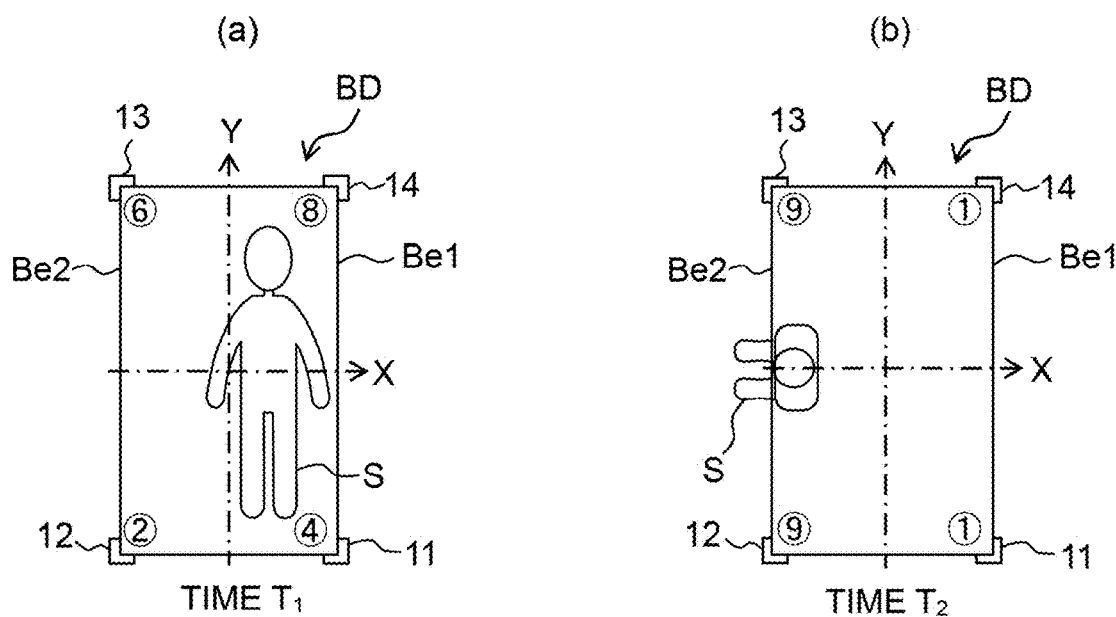
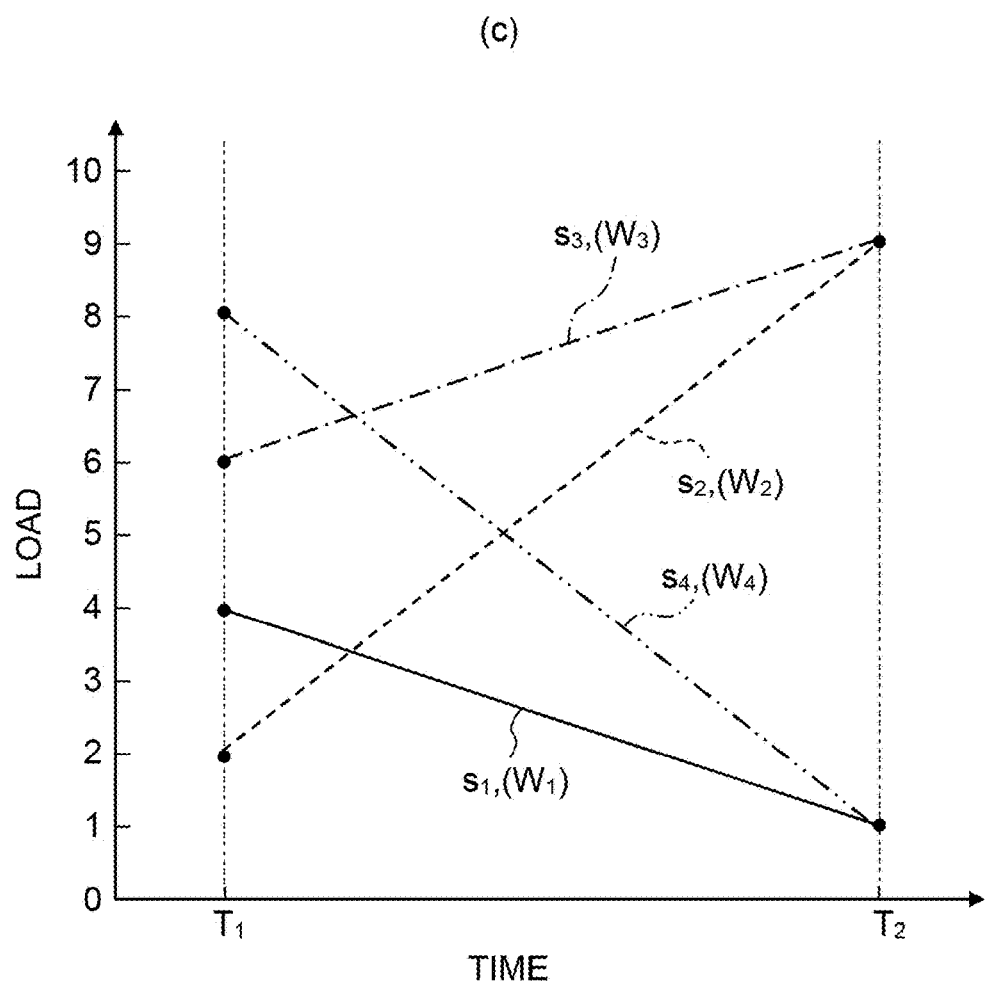

Fig. 7
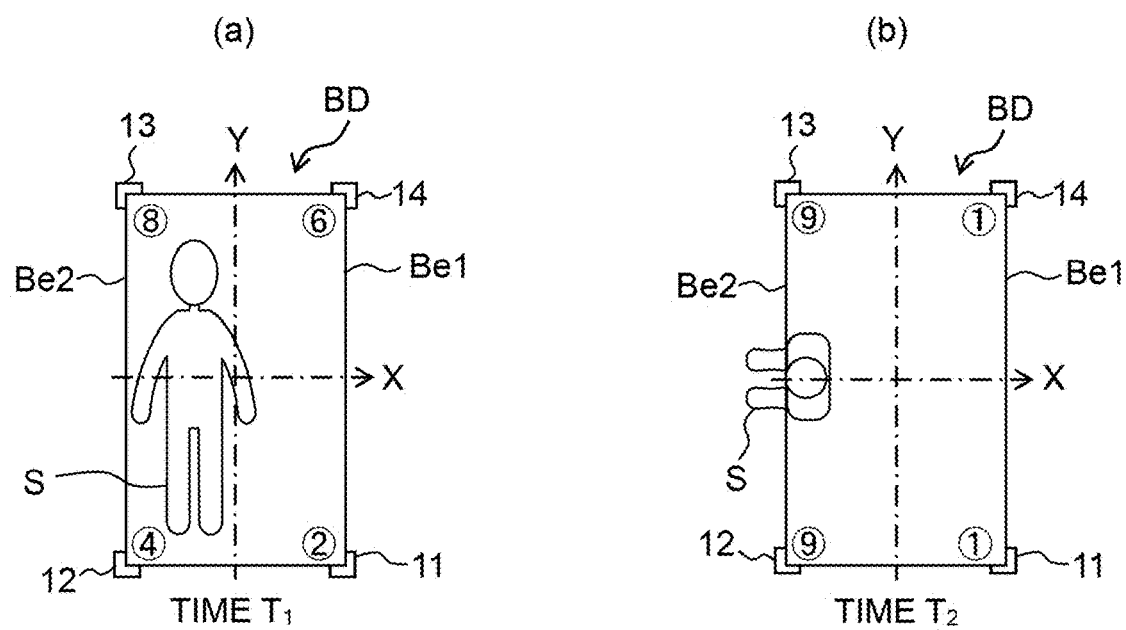
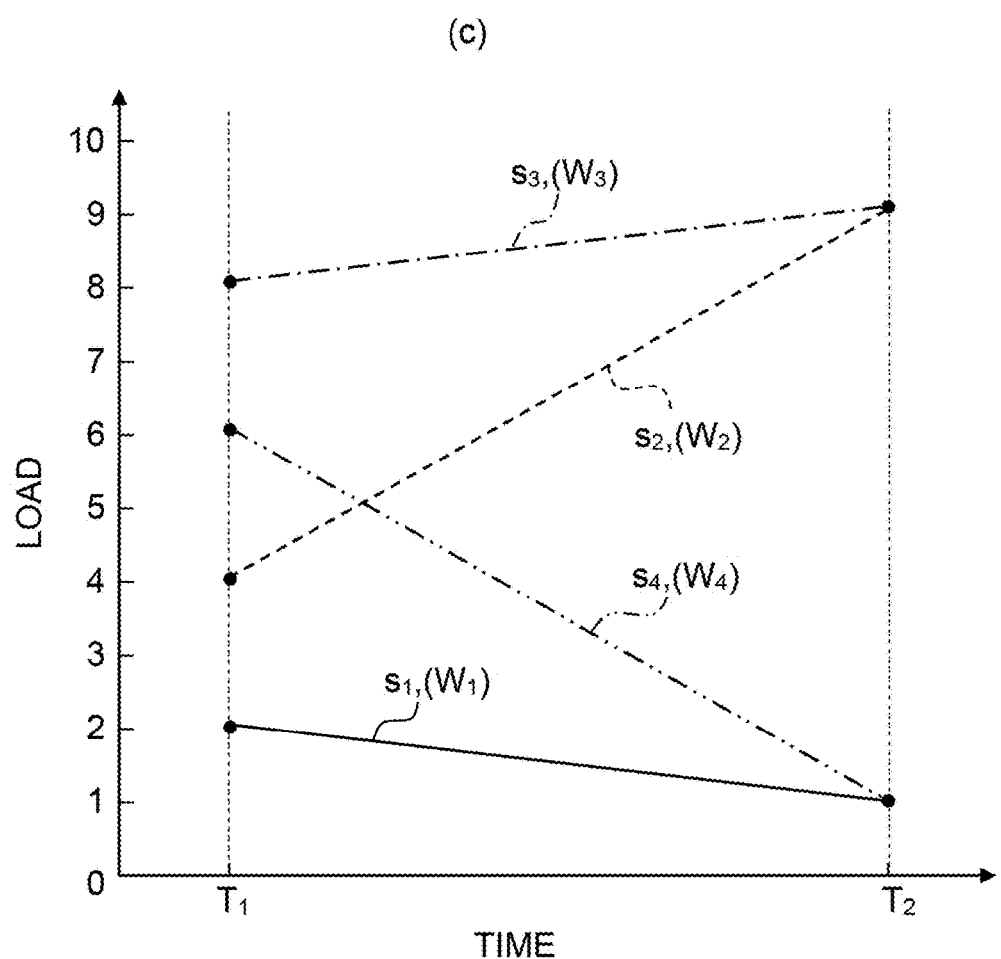

Fig. 8
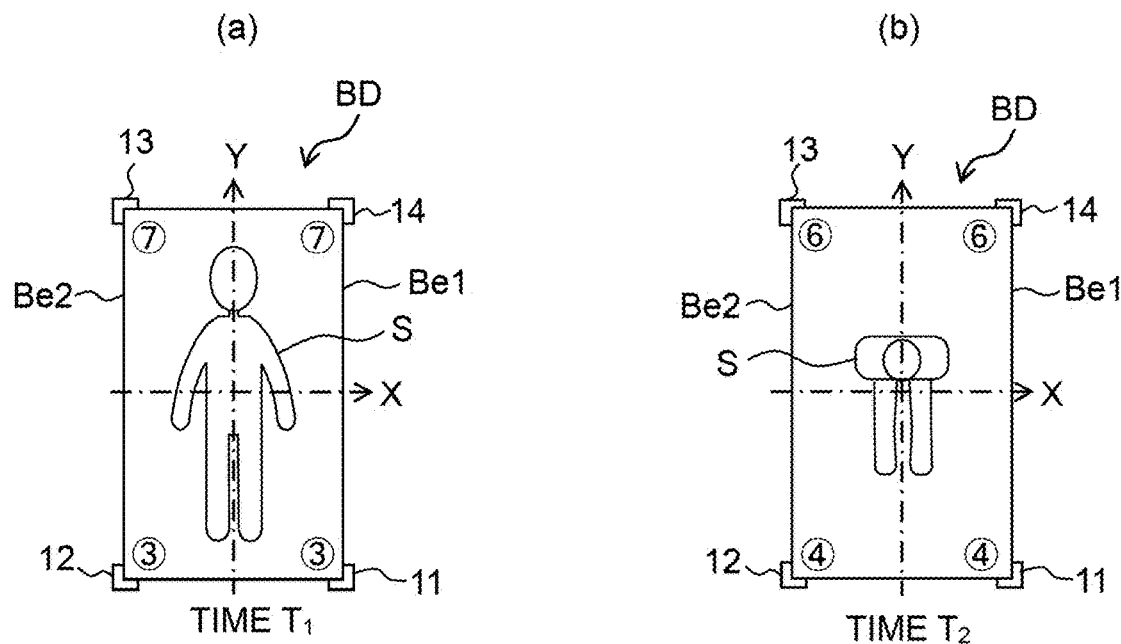
(a) TIME T₁
(b) TIME T₂
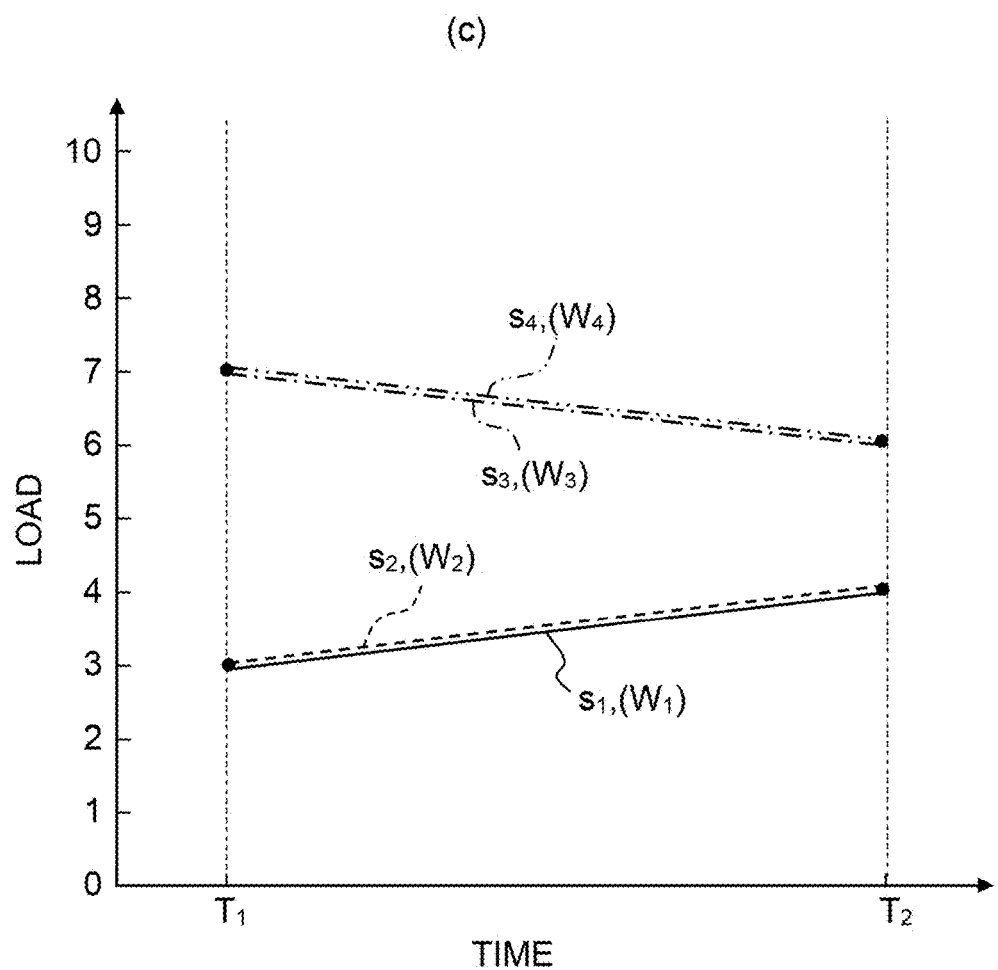
(c)

Fig. 9
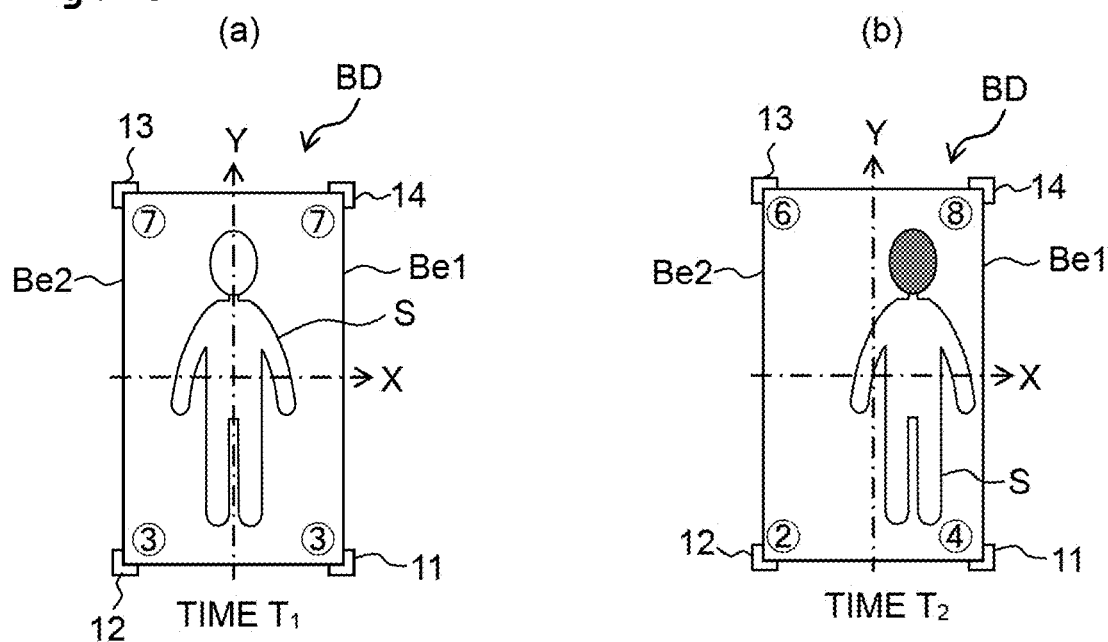
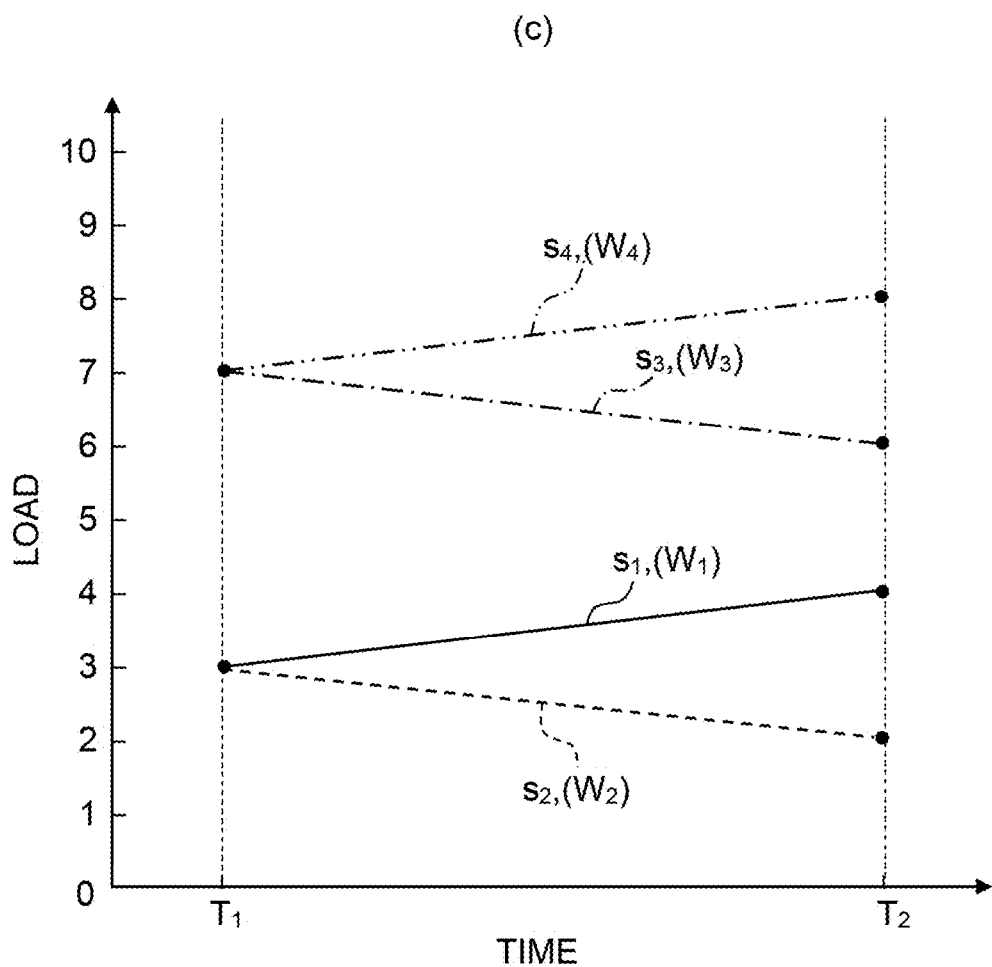

ON-BED STATE MONITORING SYSTEM

TECHNICAL FIELD

The present invention relates to an in-bed state (on-bed state) monitoring system for monitoring an in-bed state of a (human) subject on a bed on the basis of detection values of load detectors.

BACKGROUND ART

For the sites of medical treatment and caregiving, it is proposed to determine a state of a subject on the basis of such a (body weight) load of the subject on a bed as detected by load detectors. In particular, for example, it is proposed to determine whether the subject is present in the bed or absent from the bed, estimate the respiratory rate of the subject, etc., on the basis of the detected load.

Patent Literatures 1 to 3 each disclose an in-bed state monitoring system in which the load applied on the bedding portion of a bed is detected with four load detecting means and, notify the information that the in-bed position of the subject is located in an end part area of the bedding portion of the bed on the basis of a determining step carried out to fit the load values outputted from the four load detecting means into a plurality of determination formulas.

Further, Patent Literatures 1 to 3 each disclose that determination is also made on whether or not the subject is in an edge sitting posture where he or she sits at an end part of the bed.

CITATION LIST

Patent Literature 1: Japanese Patent No. 4676924
Patent Literature 2: Japanese Patent No. 4965904
Patent Literature 3: Japanese Patent No. 5086996

SUMMARY

Technical Problem

Accidents such as falls, tumbles and the like may happen to hospitalized patients, care receivers in care facilities and the like, who are disabled in the lower body when leaving the bed after reaching an edge sitting posture. Therefore, it is desired a system which is capable of detecting that the edge sitting posture is reached, and then notifying nurses, caregivers, and/or others of the detected result.

A first object of the present invention is to provide an in-bed state monitoring system capable of predicting the situation of a subject on a bed being about to reach an edge sitting posture at an earlier time.

A second object of the present invention is to provide the in-bed state monitoring system capable of determining that the subject on the bed has reached the edge sitting posture at a higher precision.

Solution to the Problem

According to a first aspect of the present invention, there is provided an in-bed state monitoring system for monitoring an in-bed state of a subject on a bed, the system including:
four load detectors which are configured to be placed at four corners of the bed to detect a load of the subject;
and an edge sitting posture determining unit configured to predict that the subject is reaching a state of edge sitting posture based on a change in a magnitude relation between detection values from two load detectors, which are of the four load detectors and are placed to interpose the bed between the two load detectors in a diagonal direction of the bed.

In the in-bed state monitoring system according to the first aspect, the edge sitting posture determining unit may be configured to predict that the subject is reaching the state of edge sitting posture based on a reversal of the magnitude relation between the detection values from the two load detectors placed to interpose the bed between the two load detectors in the diagonal direction of the bed.

The in-bed state monitoring system according to the first aspect may further include a body motion determining unit configured to determine whether a body motion of the subject is present or not based on a detection value of at least one load detector of the four load detectors; and may further include a body position determining unit configured to determine a position of the subject in a width direction of the bed based on detection values of first and second load detectors, the first load detector being at least one load detector of the four load detectors and being placed at one side of the bed in the width direction of the bed, the second load detector being at least one load detector of the four load detectors and being placed at other side of the bed in the width direction of the bed.

In the in-bed state monitoring system according to the first aspect, the edge sitting posture determining unit may be configured to determine whether the subject is in the state of edge sitting posture or not based on a determination result of the body motion determining unit and a determination result of the body position determining unit.

In the in-bed state monitoring system according to the first aspect, the edge sitting posture determining unit may be configured to determine whether the subject is in the state of edge sitting posture or not based on the determination result of the body motion determining unit and the determination result of the body position determining unit, in a case that the edge sitting posture determining unit has predicted that the subject is reaching the state of the edge sitting posture.

According to a second aspect of the present invention, there is provided an in-bed state monitoring system for monitoring an in-bed state of a subject on a bed, the system including:
four load detectors which are configured to be placed at four corners of the bed to detect a load of the subject;
a body motion determining unit configured to determine whether a body motion of the subject is present or not based on a detection value of at least one load detector of the four load detectors;
a body position determining unit configured to determine a position of the subject in a width direction of the bed based on detection values of first and second load detectors, the first load detector being at least one load detector of the four load detectors and being placed at one side of the bed in the width direction of the bed, the second load detector being at least one load detector of the four load detectors and being placed at other side of the bed in the width direction of the bed; and an edge sitting posture determining unit configured to determine whether the subject is in a state of edge sitting posture or not based on a determination result of the body motion determining unit and a determination result of the body position determining unit.

The in-bed state monitoring system according to the first aspect and the second aspect may further include a notifying unit configured to carry out a notification based on a determination result of the edge sitting posture determining unit.

According to a third aspect of the present invention, there is provided a bed system including:

a bed; and the in-bed state monitoring system according to any one of the first aspect and the second aspect.

According to the in-bed state monitoring system of the present invention, it is possible to predict the situation of a subject on a bed being about to reach an edge sitting posture at an earlier time.

According to the in-bed state monitoring system of the present invention, it is possible to determine that the subject on the bed has reached the edge sitting posture at a higher precision.

BRIEF DESCRIPTION OF THE DRAWINGS

FIGS. 5(a), 5(b), and 5(c) are views for explaining a principle used to predict an edge sitting posture of a subject, depicting an aspect of variation of detection signals of the four detectors during the period from a state of lying supine of the subject in the bed center to reaching a state of edge sitting posture.

FIGS. 6(a), 6(b), and 6(c) are views for explaining the principle used to predict the edge sitting posture of the subject, depicting the aspect of variation of detection signals of the four detectors during the period from the state of lying supine of the subject in a position deviating to one side from the bed center in a width direction, to reaching the state of edge sitting posture on the other side of the bed in the width direction.

FIGS. 7(a), 7(b), and 7(c) are views for explaining the principle used to predict the edge sitting posture of the subject, depicting the aspect of variation of detection signals of the four detectors during the period from the state of lying supine of the subject in a position deviating to one side from the bed center in the width direction, to reaching the state of edge sitting posture on the same one side.

FIGS. 8(a), 8(b), and 8(c) are views for explaining the principle used to predict the edge sitting posture of the subject, depicting the aspect of variation of detection signals of the four detectors during the period from the state of lying supine of the subject in the bed center to reaching a state of sitting on the bed center with the upper body being upright.

FIGS. 9(a), 9(b), and 9(c) are views for explaining the principle used to predict the edge sitting posture of the subject, depicting the aspect of variation of detection signals of the four detectors during the period from the state of lying supine of the subject in the bed center to reaching the state of lying prone in a position deviating to one side from the bed center in the width direction.

DESCRIPTION OF EMBODIMENT

Embodiment

An explanation will be made on an in-bed state monitoring system (on-bed state monitoring system) 100 (FIG. 1) according to an embodiment of the present invention, with an example of using the above system with a bed BD (FIG. 2) to monitor an in-bed state (present-in-bed state, present-on-bed state) of a subject S on the bed BD.

In the following explanation, with the center of the cuboid bed BD (FIG. 2) as the center O, the axis X of the bed BD is defined as the axis extending in the breadthwise (widthwise) direction of the bed BD and passing through the center O, and the axis Y of the bed BD is defined as the axis extending in the lengthwise (longitudinal or up/down) direction of the bed BD and passing through the center O. In planar view of the bed BD, the positive side of the axis X is the right side of the center O of the bed BD whereas the negative side of the axis X is the left side thereof, and the positive side of the axis Y is the upper side of the center O of the bed BD whereas the negative side of the axis Y is the lower side thereof. When the subject S lies on the bed BD, generally he or she lies along the axis Y and the head is placed on the positive side and the feet are placed on the negative side in the axis-Y direction.

Figure 1:
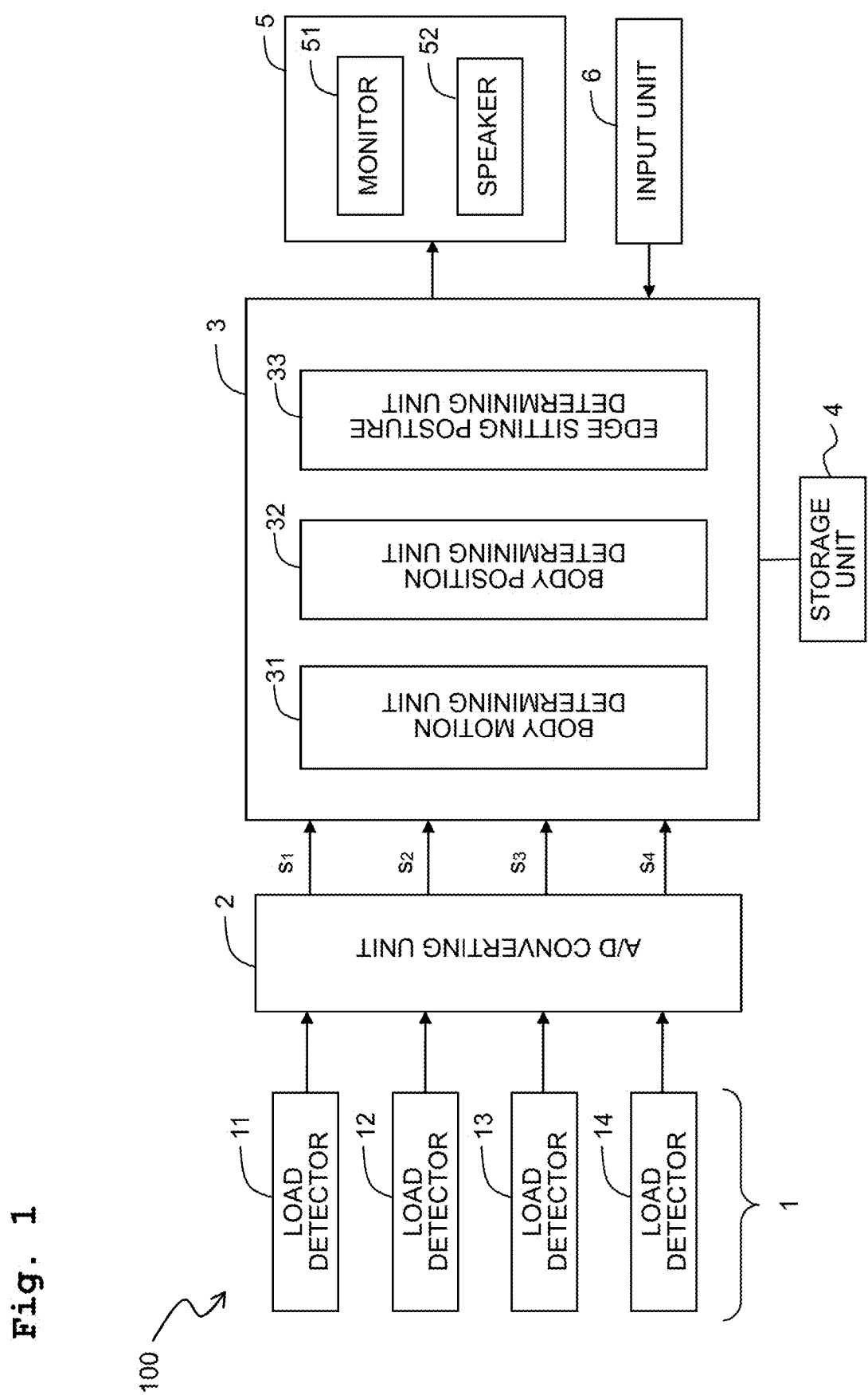
FIG. 1 is a block diagram depicting a configuration of an in-bed state monitoring system according to an embodiment of the present invention.

As shown in FIG. 1, the in-bed state monitoring system 100 of this embodiment primarily has a load detecting unit 1, a control unit 3, a storage unit 4, and a notifying unit 5. The load detecting unit 1 and the control unit 3 are connected via an A/D converting unit 2. The control unit 3 is further connected to an input unit 6.

The load detecting unit 1 includes four load detectors 11, 12, 13, and 14. Each of the load detectors 11, 12, 13, and 14 is a load detector for detecting a load by using, for example, a beam-type load cell. Such a load detector is disclosed, for example, in Japanese Patent No. 4829020 and Japanese Patent No. 4002905. Each of the load detectors 11, 12, 13, and 14 is connected to the A/D converting unit 2 by way of wiring or wirelessly.

Figure 2:
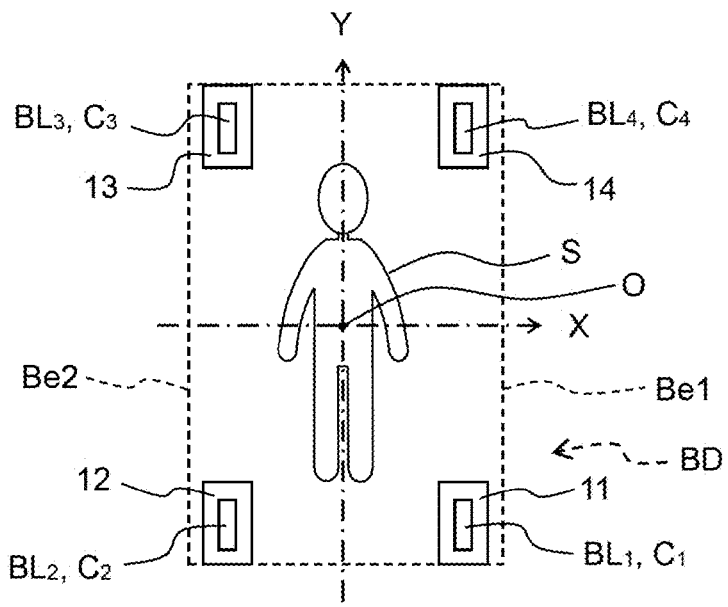
FIG. 2 is an illustrative view depicting an arrangement of load detectors for a bed.

As shown in FIG. 2, the four load detectors 11 to 14 of the load detecting unit 1 are arranged respectively under casters $C_1$, $C_2$, $C_3$, and $C_4$ fitted on the lower ends of legs $BL_1$, $BL_2$, $BL_3$, and $BL_4$ at the four corners of the bed BD used by the subject S.

The A/D converting unit 2 includes an A/D convertor connected respectively to the load detecting unit 1 and the control unit 3 by way of wiring or wirelessly, to convert analog signals from the load detecting unit 1 to digital signals.

The control unit 3 is a dedicated or general-purpose computer inside which a body motion determining unit 31, a body position determining unit 32, and an edge sitting posture (edge sitting position) determining unit 33 are constructed.

The storage unit 4 is a storage device for storing data used in the in-bed state monitoring system 100 and, for example, can use a hard disk (magnetic disk) for that purpose. The notifying unit 5 is a part for performing predetermined notifications on the basis of the output from the control unit 3, including a monitor 51 such as a liquid crystal monitor or the like for visual (image) notification, and a speaker 52 for auditory notification.

The input unit 6 is an interface for performing predetermined inputs for the control unit 3, which may be a keyboard and a mouse.

An explanation will be made on an operation of monitoring the in-bed state of the subject on the bed by using such in-bed state monitoring system 100. In this context, to monitor the in-bed state of the subject is, in particular for example, to predict a situation of the subject reaching (or being about to reach) a state of the edge sitting posture, and/or to determine whether or not the subject has reached the edge sitting posture. Note that in the present specification and the present invention, the term "(state of) edge sitting posture" means that the subject is in a state of sitting at an end (edge) of the bed in the width direction thereof. The edge sitting posture (edge sitting position) includes both of the state that the subject's feet are in contact with the floor surface under the bed and the state that subject's feet are not in contact with the floor surface.

Figure 3:
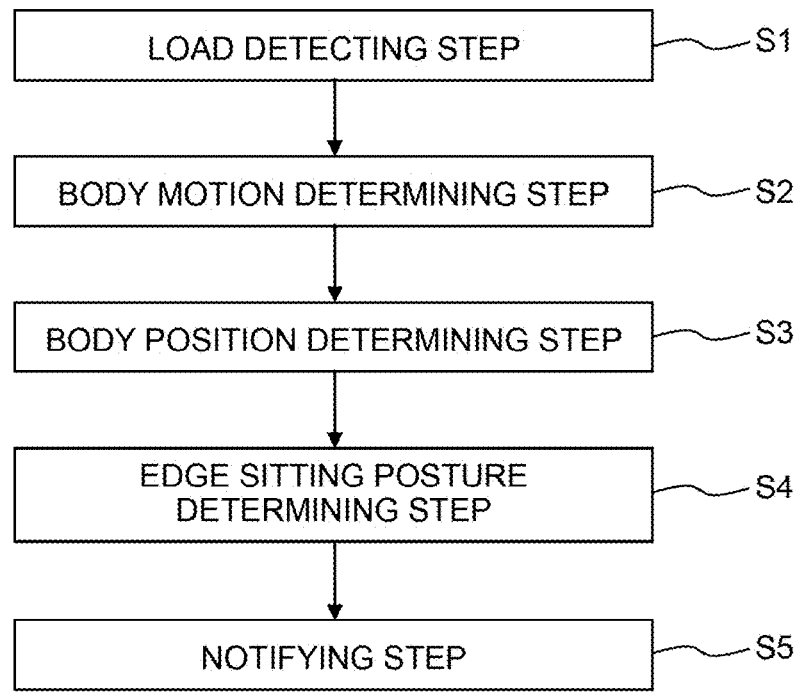
FIG. 3 is a flow chart depicting a method for monitoring an in-bed state by using the in-bed state monitoring system.

Monitoring the in-bed state of the subject by using the in-bed state monitoring system 100 includes: as depicted in the flow chart of FIG. 3, a load detecting step S1 for detecting the load of the subject; a body motion determining step S2 for determining whether or not there is a body motion of the subject on the basis of the detected load; a body position determining step S3 for determining whether or not the subject has approached an end of the bed on the basis of the detected load; an edge sitting posture determining step S4 for predicting that the subject is to reach the edge sitting posture and/or determining whether or not the subject has reached the edge sitting posture on the basis of at least one of the following determination results: the load of the subject detected in the load detecting step S1, whether or not there is a body motion of the subject determined in the body motion determining step S2, and whether or not the subject has approached an end of the bed determined in the body position determining step S3; and a notifying step S5 for performing predetermined a notification on the basis of the determination result of the edge sitting posture determining step S4.

[The Load Detecting Step]

In the load detecting step S1, the load detectors 11, 12, 13, and 14 are used to detect the load of the subject S on the bed BD. The load of the subject S on the bed BD is applied dispersively to the load detectors 11 to 14 arranged respectively under the legs $BL_1$ to $BL_4$ of the bed BD at the four corners, and is detected dispersively by the four load detectors.

Each of the load detectors 11 to 14 detects the load (a variation in load), and outputs the result as an analog signal to the A/D converting unit 2. The A/D converting unit 2 converts the analog signal into a digital signal through a sampling period of 5 milliseconds, for example, and then outputs the digital signal (to be referred to below as "load signal") to the control unit 3. Hereinafter, the term "load signals $s_1$, $s_2$, $s_3$, and $s_4$" will be used to refer respectively to the load signals obtained by the A/D converting unit 2 converting the analog signals outputted from the load detectors 11, 12, 13, and 14 into the digital format.

[The Body Motion Determining Step]

In the body motion determining step S2, a body motion determining unit 31 uses at least one of the load signals $s_1$ to $s_4$, to determine whether or not there is a body motion of subject S.

In this context, the term "body motion" refers to any motion of the subject's head, torso (body-trunk), or four limbs. The body motion does not include motions of internal organs, blood vessels and the like along with the respirations, heartbeats, and the like. As an example, the body motion can be classified into a large body motion along with the motion of the subject S in the torso (body-trunk), and a small body motion along with the motion of the subject only in the four limbs and/or the head. One example of the large body motion is turn-over, sit-up or get-up, or the like, whereas one example of the small body motion is, a motion of the hands, the feet, the head or the like during sleep.

The body motion determining unit 31 determines whether or not there is a body motion arising in the subject S on the basis of the flowing principle.

Figure 4:
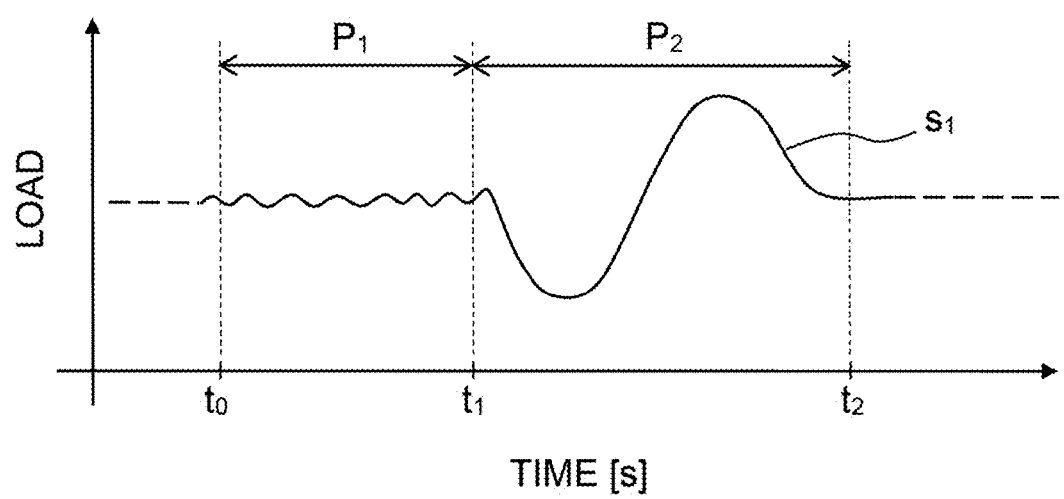
FIG. 4 is a graph schematically depicting an example of a load value detected by a load detector.

FIG. 4 depicts such a schematic waveform of the load signal $s_1$ from the load detector 11 as obtained in a predetermined period including times $t_0$, $t_1$, and $t_2$.

Within the period when the waveform depicted in FIG. 4 is obtained, in the period from the time $t_0$ to the time $t_1$ (period $P_1$), there is no body motion arising in the subject S. Therefore, the load signal $s_1$ during this period vibrates only a little, reflecting a motion of the internal organs, blood vessels and the like of the subject in accordance with the respirations and heartbeats of the subject S, such that the amount of variation is small. In other words, in the period $P_1$ when the subject S has no body motion, there is a small variation in the sampling value of the load signal $s_1$.

On the other hand, within the period when the waveform depicted in FIG. 4 is obtained, in the period from the time $t_1$ to the time $t_2$ (period $P_2$), there is a body motion arising in the subject S. In particular, the subject S moves his/her right arm. Therefore, the load signal $s_1$ during this period varies greatly, reflecting the motion of the right arm of the subject S. In other words, in the period $P_2$ when the subject S has a body motion, there is a large variation in the sampling value of the load signal $s_1$.

In this manner, the variation of the sampling value of the load signal $s_2$ from the load detector 11 becomes small in the period when the subject S has no body motion but becomes large in the period when the subject S has a body motion. Much the same is true on the load signals $s_2$, $s_2$, and $s_4$ from the load detectors 12, 13, and 14.

Therefore, the body motion determining unit 13 calculates, for at least one of the load signals $s_2$ to $s_4$ from the load detectors 11 to 14, a standard deviation σ which indicates the magnitude of variation of the sampling value included in a predetermined period (such as 5 seconds as one example), and determines whether or not there is a body motion arising in the subject S on the basis of a comparison between the calculated standard deviation σ and a predetermined threshold value $σ_{th}$.

In particular, for example, if the standard deviation σ calculated for the predetermined period is smaller in value than the predetermined threshold value $σ_{th}$, then the body motion determining unit 13 determines that there is no body motion arising in the subject S during that period. On the other hand, if the standard deviation σ calculated for the predetermined sampling period is larger in value than the predetermined threshold value $σ_{th}$, then the body motion determining unit 13 determines that there is a body motion arising in the subject S during that period. Note that whether or not the subject S has a body motion may be determined by comparing a dispersion $σ^2$ with a predetermined threshold value $σ^2_{th}$, instead of the standard deviation σ.

[The Body Position Determining Step]

In the body position determining step S3, the body position determining unit 32 determines whether or not the body position of the subject S has approached (is close to)

an end of the bed BD in the width direction (in the axis-X direction), on the basis of the load signals $s_1$ to $s_4$ from the load detectors 11 to 14.

Hereinbelow, a first bed end Be1 refers to the end of the bed BD on the positive side in the axis-X direction, whereas a second bed end Be2 refers to the end of the bed BD on the negative side in the axis-X direction (FIG. 2). Further, the first bed end Be1 and the second bed end Be2 are collectively referred to as "the bed end".

The body position determining unit 32 finds a value X by using the following formula 1, where $W_1$, $W_2$, $W_3$, and $W_4$ are the sampling values at different sampling times of the load signals $s_1$, $s_2$, $s_3$, and $s_4$ from the load detectors 11, 12, 13, and 14, respectively.

$$X=|(W_1+W_4)-(W_2+W_3)| \qquad \text{(Formula 1)}$$

Then, the body position determining unit 32 determines whether or not the subject S has approached (is close to) the bed end by using the found value X according to the following principle.

Among the load detectors 11 to 14 included in the in-bed state monitoring system 100 of this embodiment, the load detectors 11 and 14 are arranged under the legs $BL_1$ and $BL_4$ on the side of the first bed end Be1 whereas the load detectors 12 and 13 are arranged under the legs $BL_2$ and $BL_3$ on the side of the second bed end Be2.

When the subject S is positioned in the vicinity of the center O of the bed BD, because the load of the subject S is applied equally to the side of the first bed end Be1 and to the side of the second bed end Be2, the sum $(W_1+W_4)$ of the sampling values $W_1$ and $W_4$ of the load signals $s_1$ and $s_4$ from the load detectors 11 and 14 is almost equal to the sum $(W_2+W_3)$ of the sampling values $W_2$ and $W_3$ of the load signals $s_2$ and $s_3$ from the load detectors 12 and 13. Hence, the value X found with the formula 1 is almost equal to zero.

On the other hand, as the subject S approaches the first bed end Be1, the sampling values $W_1$ and $W_4$ of the load signals $s_1$ and $s_4$ from the load detectors 11 and 14 increase accordingly whereas the sampling values $W_2$ and $W_3$ of the load signals $s_2$ and $s_3$ from the load detectors 12 and 13 decrease accordingly. On this occasion, the value X found with the formula 1 increases accordingly. Likewise, as the subject S approaches the second bed end Be2, the sampling values $W_2$ and $W_3$ of the load signals $s_2$ and $s_2$ from the load detectors 12 and 13 increase accordingly whereas the sampling values $W_1$ and $W_4$ of the load signals $s_2$ and $s_4$ from the load detectors 11 and 14 decrease accordingly. On this occasion, too, the value X found with the formula 1 increases accordingly.

Based on such a relation between the value X and the position of the subject S on the bed BD in the axis-X direction, the body position determining unit 32 determines whether or not the subject S has approached the bed end. In particular, the body position determining unit 32 compares the value X found with the formula 1 with a predetermined threshold value $X_{th}$, to determine that the subject S has approached (is close to) the bed end at the point when the value X exceeds the predetermined threshold value $X_{th}$.

The predetermined threshold value $X_{th}$ can be set as appropriate. If it is desirable to determine that the subject has approached the bed end at an earlier point of time (that is, at a point of time when there is a comparatively long distance between the subject S and the bed end), then the predetermined threshold value $X_{th}$ is set to a comparatively small value. Conversely, if it is desirable to determine that the subject has approached the bed end at an later point of time (that is, at a point of time when the distance between the subject S and the bed end has become comparatively short), then the predetermined threshold value $X_{th}$ is set to a comparatively large value.

Note that because a rigid body is most stable when supported at three points, the bed BD may also fall into a more or less three-point supported state (that is, the bed BD is no longer supported uniformly by the legs $BL_1$ to $BL_4$ at the four corners, but three of the four legs increase in the share of support whereas the other one decreases in the share of support). On this occasion, the load of the bed BD with the subject S thereupon is applied more to three of the load detectors 11 to 14 under the legs $BL_1$ to $BL_4$ at the four corners, but less to the other one. However, the body position determining unit 32 of this embodiment determines the body position of the subject S with the formula 1 which comprehensively uses the sampling values $W_1$ to $W_4$ of the load signals $s_1$ to $s_4$ from the load detectors 11 to 14; therefore, even if the bed BD falls into the more or less three-point supported state, it is still possible to offset (balance), to a certain degree, the possible errors arising in the values of the sampling values $W_1$ to $W_4$ due to the occurrence of the more or less three-point supported state, thereby restraining the precision of determination from decreasing.

[The Edge Sitting Posture Determining Step]

In the edge sitting posture determining step S4, first, the edge sitting posture determining unit 33 predicts a situation of the subject S being about to reach the state of edge sitting posture on the basis of the load signals $s_1$ to $s_4$ from the load detectors 11 to 14. Then, after predicting the situation of the subject S being about to reach the edge sitting posture, the edge sitting posture determining unit 33 determines whether or not the subject S has actually reached the edge sitting posture on the basis of the determination result in the body motion determining step S2 and the determination result in the body position determining step S3.

The edge sitting posture determining unit 33 predicts the situation of the subject S being about to reach the edge sitting posture on the basis of the following principle.

The inventor of the present invention has made a number of researches on the relation between the aspect of motion of the subject S on the bed BD and the aspect of variation in the load signals $s_1$ to $s_4$ from the load detectors 11 to 14 according to the motion of the subject S, in order to detect the subject S reaching the edge sitting posture at an earlier time. Then, in the course of movement of the subject S from the state of lying on the bed BD (the state of lying supine, lying recumbent, or lying prone) to the state of edge sitting posture in which he or she is sitting at the bed end (bed edge), between a pair of the load detectors arranged to interpose the bed BD therebetween along a diagonal direction (a pair of the load detectors arranged at diagonal positions of the bed BD), it was found out that a magnitude relation between the sampling values of the load signals reverses at an extremely high probability.

Based on this discovery and knowledge of the inventor of the present invention, the edge sitting posture determining unit 33 predicts the situation of the subject S being about to reach the edge sitting posture on the basis of the reversal of the magnitude relation either between the sampling value $W_1$ of the load signal $s_1$ from the load detector 11 and the sampling value $W_3$ of the load signal $s_3$ from the load detector 13, or between the sampling value $W_2$ of the load signal $s_2$ from the load detector 12 and the sampling value $W_4$ of the load signal $s_4$ from the load detector 14.

Several specific examples will be taken to show that in the course of movement of the subject S from the state of lying on the bed BD to the state of edge sitting posture in which he or she is sitting at the bed end, between a pair of the load detectors arranged to interpose the bed BD therebetween along a diagonal direction, the magnitude relation reverses between the sampling values of the load signals.

(1) Specific Example 1

As shown in FIG. 5($a$), at a time $T_1$ when the subject S is lying supine in almost the center of the bed BD in the axis-X direction to align the body axis in the axis-Y direction, the load of the subject S is applied to the load detectors 11, 12, 13, and 14 provided at the four corners of the bed BD at the ratio of approximately 3:3:7:7. Therefore, the sampling values $W_1$, $W_2$, $W_3$, and $W_4$ of the load signals $s_1$, $s_2$, $s_3$, and $s_4$ from the load detectors 11, 12, 13, and 14 are also approximately 3:3:7:7 in magnitude. The proportions of the load applied to the load detectors 11 and 12 arranged on the feet side of the subject S are smaller than proportions of the load applied to the load detectors 13 and 14 arranged on the head side of the subject S. This is because the ratio of weight between the upper half and the lower half of the human body is approximately 7:3.

As shown in FIG. 5($b$), at a time $T_2$ when the subject S is sitting at the edge of the bed in almost the center of the bed BD in the axis-Y direction at the second bed end Be2, the most part of the load of the subject S is applied to the load detectors 12 and 13 on the side of the second bed end Be2. In this context, for example, suppose that the load of the subject S is applied to the load detectors 11, 12, 13, and 14 provided at the four corners of the bed BD at the ratio of approximately 1:9:9:1. In this case, the sampling values $W_1$, $W_2$, $W_3$, and $W_4$ of the load signals $s_1$, $s_2$, $s_3$, and $s_4$ from the load detectors 11, 12, 13, and 14 are also approximately 1:9:9:1 in magnitude.

Hereinbelow, let attention be paid to the load signal $s_2$ from the load detector 12 arranged on the negative side in the axis-X direction and on the negative side in the axis-Y direction of the bed BD, and the load signal $s_4$ from the load detector 14 arranged on the positive side in the axis-X direction and on the positive side in the axis-Y direction of the bed BD (that is, at the diagonal position from the load detector 12).

At the time $T_1$ when the subject S is lying supine in the center of the bed, about 3/20 of the load of the subject S is applied to the load detector 12 provided on the feet side of the subject S while about 7/20 of the load of the subject S is applied to the load detector 14 provided on the head side of the subject S. That is, at the time $T_1$ when the subject S is lying supine in the center of the bed, more of the load is applied to the load detector 14 provided on the head side of the subject S than to the load detector 12 provided on the feet side of the subject S. Therefore, the sampling value $W_4$ of the load signal $s_4$ is larger than the sampling value $W_2$ of the load signal $s_2$ (FIG. 5($c$)).

On the other hand, at the time $T_2$ when the subject S is sitting edge at the second bed end Be2, about 9/20 of the load of the subject S is applied to the load detector 12 provided at the second bed end Be2 where the subject S is present while about 1/20 of the load of the subject S is applied to the load detector 14 provided at the first bed end Be1 where the subject S is absent. That is, at the time $T_2$ when the subject S is sitting at the edge of the bed at the second bed end Be2, more of the load is applied to the load detector 12 provided at the second bed end Be2 where the subject S is present than to the load detector 14 provided at the first bed end Be1 where the subject S is absent. Therefore, the sampling value $W_2$ of the load signal $s_2$ is larger than the sampling value $W_4$ of the load signal $s_4$ (FIG. 5($c$)).

In the above manner, in the course of movement of the subject S from the state of lying supine in the center of the bed to the state of sitting at the edge of the bed at the second bed end Be2, the magnitude relation reverses between the sampling value $W_2$ of the load signal $s_2$ of the load detector 12 and the sampling value $W_4$ of the load signal $s_4$ of the load detector 14.

FIG. 5($c$) is such a graph as to schematically depict an aspect of variation in the sampling values $W_1$ to $W_4$ of the load signals $s_1$ to $s_4$ during the period from the time $T_1$ when the subject S is lying supine in the center of the bed to the time $T_2$ when the subject is sitting at the edge of the bed at the second bed end Be2. It is recognizable, from this graph as well, that the magnitude relation reverses between the sampling value $W_2$ of the load signal $s_2$ of the load detector 12 and the sampling value $W_4$ of the load signal $s_4$ of the load detector 14, right before the point for the subject S to reach the edge sitting posture during the period from the time $T_1$ to the time $T_2$. Further, it is also recognizable that the reversal of the magnitude relation of the sampling values only arises between the sampling value $W_2$ of the load signal $s_2$ and the sampling value $W_4$ of the load signal $s_4$, but does not arise between the other sampling values.

Note that it shall be understood that likewise, in a case that the subject S is positioned sitting at the edge of the bed at the first bed end Be1 of the bed BD at the time $T_2$, the magnitude relation reverses between the sampling value $W_1$ of the load signal $s_1$ and the sampling value $W_3$ of the load signal $s_3$ during the period from the time $T_1$ to the time $T_2$.

(2) Specific Example 2

As shown in FIG. 6($a$), consider that at the time $T_1$, the subject S is lying supine at the side of the first bed end Be1 of almost the center of the bed BD in the axis-X direction to align the body axis in the axis-Y direction. In this case, compared to the case where the subject S is lying supine in almost the center of the bed BD in the axis-X direction to align the body axis in the axis-Y direction (FIG. 5($a$)), more of the load is applied to the load detectors 11 and 14 provided on the side of the first bed end Be1. In this context, for example, suppose that the load of the subject S is applied to the load detectors 11, 12, 13, and 14 at the ratio of approximately 4:2:6:8. In this case, then, the sampling values $W_1$, $W_2$, $W_3$, and $W_4$ of the load signals $s_1$, $s_2$, $s_3$, and $s_4$ are also approximately 4:2:6:8 in magnitude.

As shown in FIG. 6($b$), at a time $T_2$ when the subject S is sitting at the edge of the bed in almost the center of the bed BD in the axis-Y direction at the second bed end Be2, as described in the above specific example 1, the sampling values $W_1$, $W_2$, $W_3$, and $W_4$ of the load signals $s_1$, $s_2$, $s_3$, and $s_4$ from the load detectors 11, 12, 13, and 14 are approximately 1:9:9:1 in magnitude.

At the time $T_1$ when the subject S is lying supine at the side of the first bed end Be1 of the center of the bed, 2/20 of the load of the subject is applied to the load detector 12 provided on the feet side of the subject S while 8/20 of the load of the subject is applied to the load detector 14 provided on the head side of the subject S. That is, the sampling value $W_4$ of the load signal $s_4$ from the load detector 14 is larger than the sampling value $W_2$ of the load signal $s_2$ from the load detector 12 (FIG. 6($c$)).

On the other hand, at the time $T_2$ when the subject S is sitting at the edge of the bed at the second bed end Be2, 1/20 of the load of the subject S is applied to the load detector 14 provided at the side of the first bed end Be1 where the subject S is absent while about 9/20 of the load of the subject is applied to the load detector 12 provided at the side of the second bed end Be2 where the subject S is present. That is, then, the sampling value $W_2$ of the load signal $s_2$ from the load detector 12 is larger than the sampling value $W_4$ of the load signal $s_4$ from the load detector 14 (FIG. 6(c)).

In the above manner, in the course of movement of the subject S from the state of lying supine at the side of the first bed end Be1 of the center of the bed to the state of sitting at the edge of the bed at the second bed end Be2 as well, the magnitude relation reverses between the sampling value $W_2$ of the load signal $s_2$ from the load detector 12 and the sampling value $W_4$ of the load signal $s_4$ from the load detector 14.

FIG. 6(c) is another graph schematically depicting the aspect of variation in the sampling values $W_1$ to $W_4$ of the load signals $s_2$ to $s_4$ during the period from the time $T_1$ to the time $T_2$. It is recognizable, from this graph as well, that the magnitude relation reverses between the sampling value $W_2$ of the load signal $s_2$ of the load detector 12 and the sampling value $W_4$ of the load signal $s_4$ of the load detector 14, right before the point for the subject S to reach the edge sitting posture during the period from the time $T_1$ to the time $T_2$.

(3) Specific Example 3

As shown in FIG. 7(a), consider that at the time $T_1$, the subject S is lying supine at the side of the second bed end Be2 of almost the center of the bed BD in the axis-X direction to align the body axis in the axis-Y direction. In this case, compared to the case where the subject S is lying supine in almost the center of the bed BD in the axis-X direction to align the body axis in the axis-Y direction (FIG. 5(a)), more of the load is applied to the load detectors 12 and 13 provided on the side of the second bed end Be2. In this context, for example, suppose that the load of the subject S is applied to the load detectors 11, 12, 13, and 14 at the ratio of approximately 2:4:8:6. In this case, then, the sampling values $W_1$, $W_2$, $W_3$, and $W_4$ of the load signals $s_1$, $s_2$, $s_3$, and $s_4$ are also approximately 2:4:8:6 in magnitude.

As shown in FIG. 7(b), at a time $T_2$ when the subject S is sitting in almost the center of the bed BD in the axis-Y direction at the second bed end Be2, as described in the above specific example 1, the sampling values $W_1$, $W_2$, $W_3$, and $W_4$ of the load signals $s_1$, $s_2$, $s_3$, and $s_4$ from the load detectors 11, 12, 13, and 14 are approximately 1:9:9:1 in magnitude.

At the time $T_1$ when the subject S is lying supine at the side of the second bed end Be2 of the center of the bed, 4/20 of the load of the subject is applied to the load detector 12 provided on the feet side of the subject S while 6/20 of the load of the subject is applied to the load detector 14 provided on the head side of the subject S. That is, the sampling value $W_4$ of the load signal $s_4$ from the load detector 14 is larger than the sampling value $W_2$ of the load signal $s_2$ from the load detector 12 (FIG. 7(c)).

On the other hand, at the time $T_2$ when the subject S is sitting at the edge of the bed at the second bed end Be2, 1/20 of the load of the subject S is applied to the load detector 14 provided at the side of the first bed end Be1 where the subject S is absent while about 9/20 of the load of the subject is applied to the load detector 12 provided at the side of the second bed end Be2 where the subject S is present. That is, then, the sampling value $W_2$ of the load signal $s_2$ from the load detector 12 is larger than the sampling value $W_4$ of the load signal $s_4$ from the load detector 14 (FIG. 7(c)).

In the above manner, in the course of movement of the subject S from the state of lying supine at the side of the second bed end Be2 of the center of the bed to the state of sitting at the edge of the bed at the second bed end Be2 as well, the magnitude relation reverses between the sampling value $W_2$ of the load signal $s_2$ from the load detector 12 and the sampling value $W_4$ of the load signal $s_4$ from the load detector 14.

FIG. 7(c) is another graph schematically depicting the aspect of variation in the sampling values $W_1$ to $W_4$ of the load signals $s_2$ to $s_4$ during the period from the time $T_1$ to the time $T_2$. From this graph, it is also recognizable that the magnitude relation reverses between the sampling value $W_2$ of the load signal $s_2$ of the load detector 12 and the sampling value $W_4$ of the load signal $s_4$ of the load detector 14, right before the point for the subject S to reach the edge sitting posture during the period from the time $T_1$ to the time $T_2$. Further, it is also recognizable that the reversal of the magnitude relation of the sampling values only arises between the sampling value $W_2$ of the load signal $s_2$ and the sampling value $W_4$ of the load signal $s_4$, but does not arise between the other sampling values.

Other than the cases exemplified in the specific examples 1 to 3, there are extremely large numbers of cases where the magnitude relation exchanges between the sampling values of the load signals of a pair of load detectors arranged at diagonal positions of the bed BD, right before the point for the subject S to reach the edge sitting posture within the period when subject S moves from the state of lying on the bed BD (the state of lying supine, lying recumbent, or lying prone) to the state of edge sitting posture in which he or she is sitting at the edge of the bed. This is because the sampling value of a first load detector, provided to locate on the feet side of the subject when the subject S is lying and locate on the side of the subject being present when the subject S is sitting at the edge of the bed, increases greatly during the period in which the subject moves to the edge sitting posture; and the sampling value of a second load detector, provided to locate on the head side of the subject when the subject S is lying and locate on the side of the subject being absent when the subject S is sitting at the edge of the bed (that is, the second load detector is arranged at the diagonal position of the bed BD from the first load detector), decreases greatly during the period in which the subject moves to the edge sitting posture.

Further, in the specific examples 1 to 3, with the subject S lying on the bed BD, the center of gravity of the subject S is positioned on the positive side of the bed BD in the axis-Y direction. However, suppose that with the subject S lying on the bed BD, the center of gravity of the subject S is positioned on the negative side in the axis-Y direction. Then, within the period in which the subject S moves to the state of sitting at the edge of the bed at the second bed end Be2 in almost the center in the axis-Y direction, the magnitude relation reverses between the sampling value $W_1$ of the load signal $s_1$ of the load detector 11 and the sampling value $W_3$ of the load signal $s_3$ of the load detector 13.

Note that the edge sitting posture determining unit 33 of the in-bed state monitoring system 100 of this embodiment may predict that the subject S is reaching the edge sitting posture at the point when the sampling values of the load signals conform with each other between a pair of load detectors arranged to interpose the bed BD along a diagonal direction (a pair of load detectors arranged at diagonal positions of the bed BD). In the present specification and in the present invention, the expression "predicting that the subject is reaching a state of edge sitting posture based on a change in a magnitude relation between detection values (signal values; sampling values) from two load detectors" includes both of predicting the state of edge sitting posture based on the reversal of the detection values from the two load detectors and predicting the state of edge sitting posture based on the conformation of the detection values from the two load detectors.

Further, the conformation and the reversal of the magnitude relation between the load signal $s_2$ and the load signal $s_4$, such as shown in FIG. 5(c), FIG. 6(c), and FIG. 7(c), can be taken as such a phenomenon, for example, that a standard deviation between the sampling value $W_2$ of the load signal $s_2$ at a predetermined time T between the time $T_1$ and the time $T_2$, and the sampling value $W_4$ of the load signal $s_4$ at the time T decreases as time proceeds from the time $T_1$ toward the time $T_2$, and then increases again. In this manner, the expression "predicting that the subject is reaching a state of edge sitting posture based on a change in a magnitude relation between detection values (signal values; sampling values) from two load detectors" described in the present invention also includes the case where the conformation and the reversal of the detection values from two load detectors are taken with such a different point of view as, for example, the change in standard deviation between the two detection values, and predicts the edge sitting posture on the basis of such change.

Next, it will be shown, referring to comparative examples 1 and 2, that in the course of the subject S gets up from the state of being lying on the bed BD to the state of sitting up without moving in the width direction of the bed, and in the course of the subject S turning over on the bed BD, such reversal as shown in the specific examples 1 to 3 does not arise in the magnitude relation of the sampling values.

(4) Comparative Example 1 (Getting Up)

As shown in FIG. 8(a), at the time $T_1$ when the subject S is lying supine in almost the center of the bed BD in the axis-X direction to align the body axis in the axis-Y direction, as described in the specific example 1, the sampling values $W_1$, $W_2$, $W_3$, and $W_4$ of the load signals $s_1$, $s_2$, $s_3$, and $s_4$ from the load detectors 11, 12, 13, and 14 are approximately 3:3:7:7 in magnitude.

Consider that the subject S shown in FIG. 8(a) has got up and, at the time $T_2$, is sitting upright in almost the center of the bed BD in the axis-X direction (FIG. 8(b)). In this case, compared to the case where the subject S is lying supine (FIG. 8(a)), more of the load is applied to the load detectors 11 and 12 provided on the feet side of the subject S. In this context, for example, suppose that the load of the subject S is applied to the load detectors 11, 12, 13, and 14 at the ratio of approximately 4:4:6:6. In this case, then, the sampling values $W_1$, $W_2$, $W_3$, and $W_4$ of the load signals $s_1$, $s_2$, $s_3$, and $s_4$ are also approximately 4:4:6:6 in magnitude.

At the time $T_1$ when the subject S is lying supine in almost the center of the bed BD in the axis-X direction, 3/20 of the load of the subject is applied to the load detectors 11 and 12 provided on the feet side of the subject S while 7/20 of the load of the subject is applied to the load detectors 13 and 14 provided on the head side of the subject S. At the time $T_2$ when the subject S is sitting upright in almost the center of the bed BD in the axis-X direction, 4/20 of the load of the subject is applied to the load detectors 11 and 12 provided on the feet side of the subject S while 6/20 of the load of the subject is applied to the load detectors 13 and 14 provided on the head side of the subject S. In this manner, in the comparative example 1, the magnitude relation of the sampling values neither reverses between the pair of load detectors 11 and 13 nor reverses between the pair of load detectors 12 and 14, provided at the diagonal positions of the bed BD.

FIG. 8(c) is another graph schematically depicting the aspect of variation in the sampling values $W_1$ to $W_4$ of the load signals $s_1$ to $s_4$ during the period from the time $T_1$ to the time $T_2$. From this graph as well, it is recognizable that the magnitude relation neither reverses (changes) between the sampling value $W_1$ of the load signal $s_1$ of the load detector 11 and the sampling value $W_3$ of the load signal $s_3$ of the load detector 13, nor reverses (changes) between the sampling value $W_2$ of the load signal $s_2$ of the load detector 12 and the sampling value $W_4$ of the load signal $s_4$ of the load detector 14.

(5) Comparative Example 2 (Turning Over)

As shown in FIG. 9(a), at the time $T_1$ when the subject S is lying supine in almost the center of the bed BD in the axis-X direction to align the body axis in the axis-Y direction, as described in the specific example 1, the sampling values $W_1$, $W_2$, $W_3$, and $W_4$ of the load signals $s_1$, $s_2$, $s_3$, and $s_4$ from the load detectors 11, 12, 13, and 14 are approximately 3:3:7:7 in magnitude.

Consider the case where the subject S shown in FIG. 9(a) has turned over and, at the time $T_2$, is lying prone to align the body axis along the axis-Y direction at the side of the first bed end Be1 of almost the center of the bed BD in the axis-X direction (FIG. 9(b)). In this case, for example, the situation is almost the same as that of the aforementioned specific example 2 at the time $T_1$ except for the difference between lying supine and lying prone. Therefore, the sampling values $W_1$, $W_2$, $W_3$, and $W_4$ of the load signals $s_1$, $s_2$, $s_3$, and $s_4$ from the load detectors 11, 12, 13, and 14 are approximately 4:2:6:8 in magnitude.

At the time $T_1$ when the subject S is lying supine in almost the center of the bed BD in the axis-X direction, 3/20 of the load of the subject is applied to the load detectors 11 and 12 provided on the feet side of the subject S while 7/20 of the load of the subject is applied to the load detectors 13 and 14 provided on the head side of the subject S. At the time $T_2$ when the subject S is lying prone at the side of the first bed end Be1 of the center of the bed BD in the axis-X direction, 4/20 and 2/20 of the load of the subject is applied respectively to the load detectors 11 and 12 provided on the feet side of the subject S while 6/20 and 8/20 of the load of the subject is applied respectively to the load detectors 13 and 14 provided on the head side of the subject S. In this manner, in the comparative example 2, the magnitude relation of the sampling values neither reverses between the pair of load detectors 11 and 13 nor reverses between the pair of load detectors 12 and 14, provided at the diagonal positions of the bed BD.

FIG. 9(c) is another graph schematically depicting the aspect of variation in the sampling values $W_1$ to $W_4$ of the load signals $s_1$ to $s_4$ during the period from the time $T_1$ to the time $T_2$. From this graph as well, it is recognizable that the magnitude relation neither reverses (changes) between the sampling value $W_1$ of the load signal $s_1$ from the load detector 11 and the sampling value $W_3$ of the load signal $s_3$ from the load detector 13, nor reverses (changes) between the sampling value $W_2$ of the load signal $s_2$ from the load detector 12 and the sampling value $W_4$ of the load signal $s_4$ from the load detector 14.

After predicting the situation of the subject S being about to reach the edge sitting posture on the basis of the load signals $s_1$ to $s_4$ from the load detectors 11 to 14, the edge sitting posture determining unit 33 determines whether or not the subject S has actually reached the edge sitting posture. This determination is, in particular, carried out in the following manner.

If the body motion determining unit 31 determines in the body motion determining step S2 that the subject S has a body motion, then the edge sitting posture determining unit 33 receives that determination result and places a flag of "Body Motion" on. Further, if the body position determining unit 32 determines in the body position determining step S3 that the subject S has approached the bed end, then the edge sitting posture determining unit 33 receives that determination result and places a flag of "Bed End" on.

After predicting the situation of the subject S being about to reach the edge sitting posture, the edge sitting posture determining unit 33 confirms whether or not the "Body Motion" flag and the "Bed End" flag are on. Then, if both of the "Body Motion" flag and the "Bed End" flag are on or turned on, then the edge sitting posture determining unit 33 determines that the subject S has reached the edge sitting posture.

[Notifying Step]

In the notifying step S5, the notifying unit 5 notifies the nurses, caregivers, and/or others who are the users of the in-bed state monitoring system 100 of the results of the prediction and determination of the edge sitting posture determining unit 33.

The notification may be carried out by the notifying unit 5 in various forms including the visual notification using the monitor 51 and/or the auditory notification using the speaker 52. As one example, at each of the point of predicting the situation of the subject S being about to reach the edge sitting posture and the point of determining that the subject S has reached the edge sitting posture, the information therefor is displayed on the monitor 51 with an icon or the like. At the same time, some kind of notifying sound may be emitted from the speaker 52.

The notification carried out at the point of determining that the subject S has reached the edge sitting posture may give an impression of higher degree of emergency, compared to the notification carried out at the point of predicting the situation of the subject S being about to reach the edge sitting posture. For example, if the notification is visual, then the former may use red color for its icon whereas the latter may use yellow color for its icon, etc.

Nurses, caregivers, and/or others can head for the bed BD according to the notification made by the notifying unit 5. Then, after confirming the situation of the subject S (that is, a hospitalized patient, care receiver in a care facility, or another) having reached the edge sitting posture, it is possible to help him or her stand up, move to the wheelchair, etc., as necessary.

Next, an explanation will be made on an example of actual predicting of the edge sitting posture and actual determining of the edge sitting posture, by using the in-bed state monitoring system 100 of this embodiment.

This example shows the following aspect of variation in the actual posture of the subject S.

(1) Time 0 sec to time 3.0 sec: Lying supine with the body axis being a little inclined clockwise to the axis Y, in the center of the bed BD in the axis-X direction.
(2) Time 3.0 sec: Start to move toward the edge sitting posture.
(3) Time 4.5 sec to time 5.0 sec or so: Reach the edge sitting posture, sitting at the second bed end Be2.
(4) Time 6.3 sec: Stand up and leave the bed.

Figure 10:
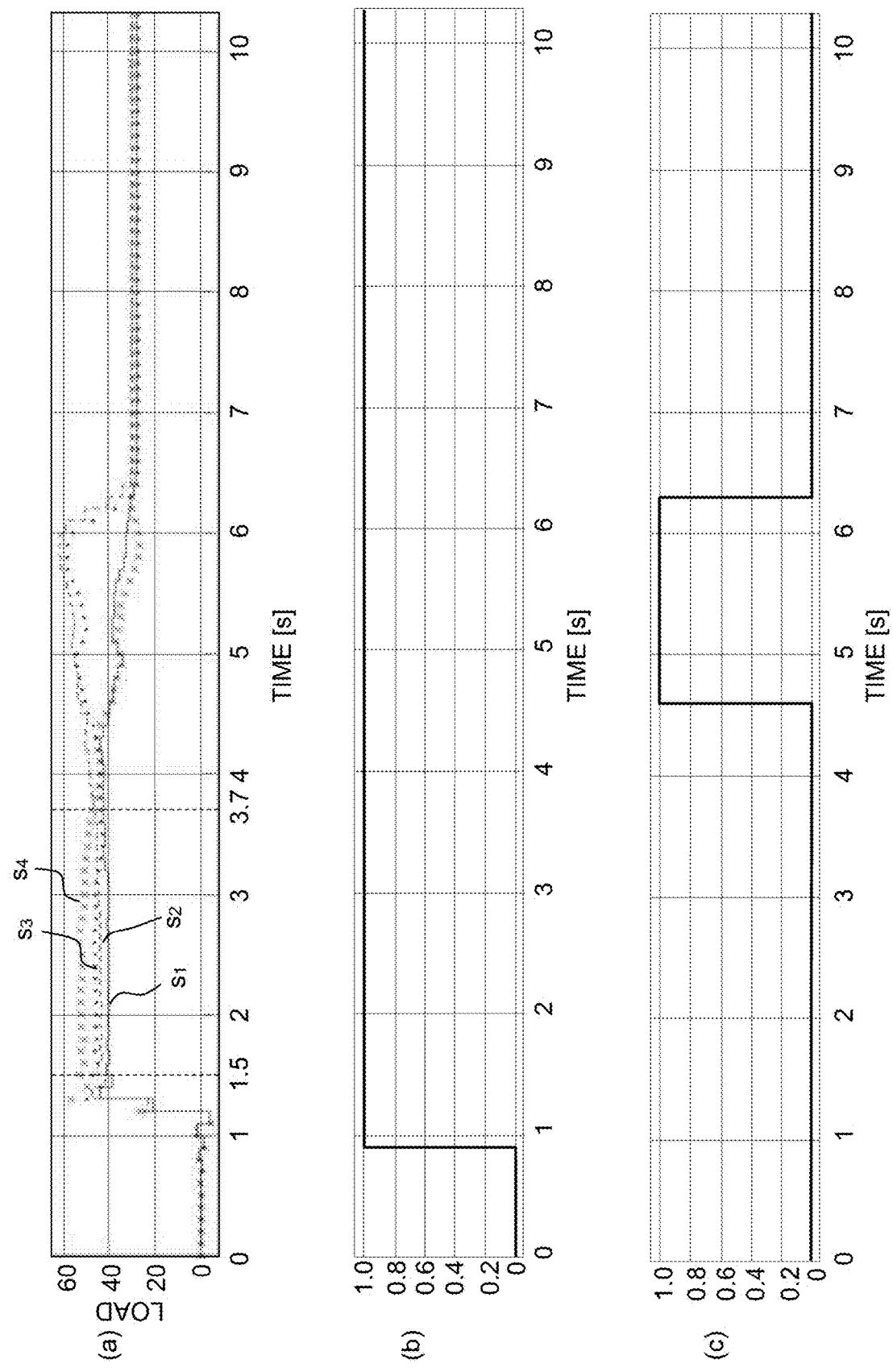
FIG. 10(a) is an example of edge sitting posture prediction performed by using the in-bed state monitoring system of the embodiment, and examples of load signals $s_1$, $s_2$, $s_3$, and $s_4$ used to determine the edge sitting posture.
FIGS. 10(b) and 10(c) depict a determination result of a body motion determining unit and a determination result of a body position determining unit, during the period when the load signals of FIG. 10(a) are obtained.

The graph of FIG. 10(a) shows the aspect of variation in the load signals $s_1$ to $s_4$ from the load detectors 11 to 14 during the period of the subject S moving in the above manner. In the graph of FIG. 10(a), during the period from the time 0 sec to the time 1.5 sec, the signal is distorted due to the startup of the in-bed state monitoring system 100, and therefore the data are ineffective.

From the graph of FIG. 10(a), it is recognizable that during the period from the time 1.5 sec to the time 3.0 sec, in which the subject S was lying supine at the center of the bed BD, each of the load signals $s_1$ to $s_4$ is stable. Further, it is also recognizable that during this period, the load signal $s_3$ and $s_4$ from the load detectors 13 and 14 positioned on the head side of the subject S are larger (in value) than the load signal $s_1$ and $s_2$ from the load detectors 11 and 12 positioned on the feet side of the subject S; the load signal $s_2$ and $s_4$ are larger than the load signal $s_1$ and $s_3$ because the body axis of the subject S is inclined to the axis Y.

Further, from FIG. 10(a), it is recognizable that at the point of 3.7 sec or so right after the subject S starts to move toward the edge sitting posture, the magnitude relation reverses between the value of the load signal $s_2$ from the load detectors 12 and the value of the load signal $s_4$ from the load detectors 14.

FIG. 10(b) and FIG. 10(c) respectively show the result of the body motion determining unit 31 determining whether or not there is a body motion of the subject S, and the result of the body position determining unit 32 determining whether or not the subject S has approached the bed end, during the period of the subject S moving in the above manner.

In the graph of FIG. 10(b), the "1" on the vertical axis means that the "Body Motion" flag is on in the edge sitting posture determining unit 33, and the "0" means that the "Body Motion" flag is not on in the edge sitting posture determining unit 33, respectively. The body motion determining unit 31 determines that there is a body motion over the entire period from the time 0 sec to the time 10 sec. This can be improved by adjusting a threshold value $\sigma_{th}$ compared with the standard deviation $\sigma$ for determining whether or not there is a body motion. In particular, for example, by adjusting the threshold value $\sigma_{th}$ appropriately to a little larger value, it is possible to obtain such a determination result as "there is a body motion" only in the period from the time 3 sec to the time 6.3 sec in which the subject S moves from the state of lying supine to the state of edge sitting and then leaves the bed.

In the graph of FIG. 10(c), the "1" on the vertical axis means that the "Bed End" flag is on in the edge sitting posture determining unit 33, and the "0" means that the "Bed End" flag is not on in the edge sitting posture determining unit 33, respectively. From FIG. 10(c), it is recognizable that the "Bed End" flag was on during the period from the time 4.5 sec to the time 5.0 sec or so in which the subject S has reached the edge sitting posture sitting at the second bed end Be2, to the time 6.3 sec when the subject S has left the bed.

The in-bed state monitoring system 100 predicted the situation of the subject S being about to reach the edge sitting posture at the time 3.7 sec, and then determined that the subject S has reached the edge sitting posture at the time 4.7 sec, on the basis of the load signals $s_1$ to $s_4$ depicted in FIG. 10(a) and the determination results of the body motion determining unit 31 and the body position determining unit 32 depicted in FIGS. 10(b) and 10(c). That is, the in-bed state monitoring system 100 made a correct prediction and determination according to the aspect of variation in the actual posture of the subject S as described above.

The effects of the in-bed state monitoring system 100 of this embodiment are summarized as follows.

The in-bed state monitoring system 100 of this embodiment is capable of predicting the situation of the subject S being about to reach the edge sitting posture before the subject S has actually reached the edge sitting posture, on the basis of the load signals $s_1$ to $s_4$ from the load detectors 11 to 14. Therefore, according to the in-bed state monitoring system 100 of this embodiment, it is possible to notify the nurses, caregivers, and/or others who are the users of the in-bed state monitoring system 100 of the situation at an earlier time and, based on this notification, it is possible for the nurses, caregivers, and/or others to help the hospitalized patients and/or others on the bed BD in a more appropriate manner. By virtue of this, it is possible to more reliably prevent accidents such as falls, tumbles and the like which may be happen when the hospitalized patients and/or others are leaving the bed.

The in-bed state monitoring system 100 of this embodiment determines whether or not the subject S has reached the edge sitting posture after predicting the situation of the subject S being about to reach the edge sitting posture on the basis of the load signals $s_1$ to $s_4$ from the load detectors 11 to 14. In this manner, because consideration is made also on the history of the load variation before the subject S reaches the edge sitting posture for determining the edge sitting posture, the determination has a high precision.

Further, the in-bed state monitoring system 100 of this embodiment takes into consideration not only the result of the body position determining unit 32 determining whether or not the subject S has approached the bed end but also the result of the body motion determining unit 31 determining whether or not the subject S is performing a body motion, for determining whether or not the subject S has reached the edge sitting posture. Because consideration is made on whether or not there is a body motion in the above manner for the determination, it is possible to carry out the determination at a higher precision by way of distinguishing the case where the subject S has actually reached the edge sitting posture from the case where, for example, the subject S is sleeping in the vicinity of the bed end without any body motion.

The in-bed state monitoring system 100 of this embodiment uses the load detectors 11 to 14 arranged under the legs $BL_1$ to $BL_4$ of the bed BD to determine the in-bed state of the subject S. Therefore, it is not necessary to attach any measuring device to the body of the subject S so that the subject S will not feel discomfort and a sense of incongruity.

MODIFIED EMBODIMENTS

It is possible to use the following modified embodiments with respect to the in-bed state monitoring system 100 of the above embodiment.

In the in-bed state monitoring system 100 of the above embodiment, the body motion determining unit 31 selects at least any one of the load signals $s_1$ to $s_4$ from the load detectors 11 to 14 to calculate the standard deviation σ for the selected load signal(s). However, without being limited to that, the body motion determining unit 31 may calculate the standard deviation σ for all of the load signals $s_1$ to $s_4$ and, in this case for example, the body motion determining unit 31 may determine whether or not the subject S has a body motion by way of comparing the maximal value of the calculated standard deviations σ with the predetermined threshold value $\sigma_{th}$.

In the in-bed state monitoring system 100 of the above embodiment, the body motion determining unit 31 uses at least one of the load signals $s_1$ to $s_4$ as it is from the A/D converting unit 2 to calculate the standard deviation σ. However, without being limited to that, the body motion determining unit 31 may perform a down sampling for at least one of the load signals $s_1$ to $s_4$ to calculate the standard deviation σ thereafter.

In the in-bed state monitoring system 100 of the above embodiment, the body motion determining unit 31 may find the standard deviation σ by using the signal after carrying out a motion averaging process over 15 seconds, for example, to block the DC component for at least one of the load signals $s_1$ to $s_4$. In the in-bed state monitoring system 100 of the above embodiment, the body motion determining unit 31 may find the standard deviation σ by using the signal after carrying out both the above down sampling and the above motion averaging process.

In the in-bed state monitoring system 100 of the above embodiment, the body motion determining unit 31 may determine whether or not there is a body motion without calculating the standard deviation σ.

In particular, for example, if there is a body motion arising in the subject S, then the position of the center of gravity G of the subject S moves accordingly. The amount of this movement is larger than the amount of movement of the center of gravity G due to the motion of the internal organs, blood vessels and the like in accordance with the respirations and heartbeats. Therefore, the body motion determining unit 31 may calculate the position of the center of gravity G of the subject S and a center of gravity locus GT which is a temporal change thereof, by using the load signals $s_1$ to $s_4$. Then, during a predetermined period, if the center of gravity G moves beyond a predetermined distance, then the body motion determining unit 31 may determine that there is a body motion in the subject S.

In the in-bed state monitoring system 100 of the above embodiment, instead of using the formula 1, the body position determining unit 32 may determine whether or not the subject S has approached the bed end, on the basis of comparing a predetermined threshold value with the absolute value of the difference between any of the sampling values $W_1$ and $W_4$ of the load signals $s_1$ and $s_4$ from the load detectors 11 and 14 provided at the side of the first bed end Be1 and any of the sampling values $W_2$ and $W_4$ of the load signals $s_2$ and $s_3$ from the load detectors 12 and 13 provided at the side of the second bed end Be2. For example, the value X' expressed by $X'=|W|-W_2|$ also increases as the subject S is approaching the bed end. Therefore, it is possible to determine whether or not the subject S has approached the bed end on the basis of comparing the value X' with a predetermined threshold value $X'_{th}$.

In the in-bed state monitoring system 100 of the above embodiment, the body position determining unit 32 may determine whether or not the subject S has approached the bed end on the basis of the distance between the position of the center of gravity G of the subject S and the first and second bed ends Be1 and Be2.

In the in-bed state monitoring system 100 of the above embodiment, when predicting the situation of the subject S being about to reach the edge sitting posture, the edge sitting posture determining unit 33 may predict whether the subject S is about to reach the edge sitting posture at the first bed end Be1 or at the second bed end Be2 as well.

In particular, for example, the edge sitting posture determining unit 33 predicts that the subject S is about to reach the edge sitting posture at the first bed end Be1 in a case that exchange is detected in the magnitude relation between the sampling value $W_1$ of the load signal S1 from the load detector 11 and the sampling value $W_3$ of the load signal $s_3$ from the load detector 13, and predicts that the subject S is about to reach the edge sitting posture at the second bed end Be2 in a case that exchange is detected in the magnitude relation between the sampling value $W_2$ of the load signal $S_2$ from the load detector 12 and the sampling value $W_4$ of the load signal $s_4$ from the load detector 14. Further, the prediction may further take the position of the center of gravity G into referential consideration.

In the in-bed state monitoring system 100 of the above embodiment, the edge sitting posture determining unit 33 determines the edge sitting posture by using the determination result of the body motion determining unit 31 and the determination result of the body position determining unit 32 after predicting the situation of the subject S being about to reach the edge sitting posture on the basis of the load signals $s_1$ to $s_4$. However, the present invention is not limited to that.

No matter whether or not the situation of the subject S being about to reach the edge sitting posture is predicted (i.e., regardless of the prediction of reaching the edge sitting posture), the edge sitting posture determining unit 33 may confirm whether or not the "Body Motion" flag is on the basis of the determination result of the body motion determining unit 31 and whether or not the "Bed End" flag is on on the basis of the determination result of the body position determining unit 32, so as to determine that the subject S has reached the edge sitting posture in a case that both flags are on.

In the in-bed state monitoring system 100 of the above embodiment, the edge sitting posture determining unit 33 is configured to be capable of both predicting the edge sitting posture and determining the edge sitting posture. However, without being limited to that, the edge sitting posture determining unit 33 may be configured to be capable of either predicting the edge sitting posture or determining the edge sitting posture.

In the in-bed state monitoring system 100 of the above embodiment, the load detectors 11 to 14 are not limited to load sensors using beam-type load cells but, for example, force sensors are also usable.

Figure 11:
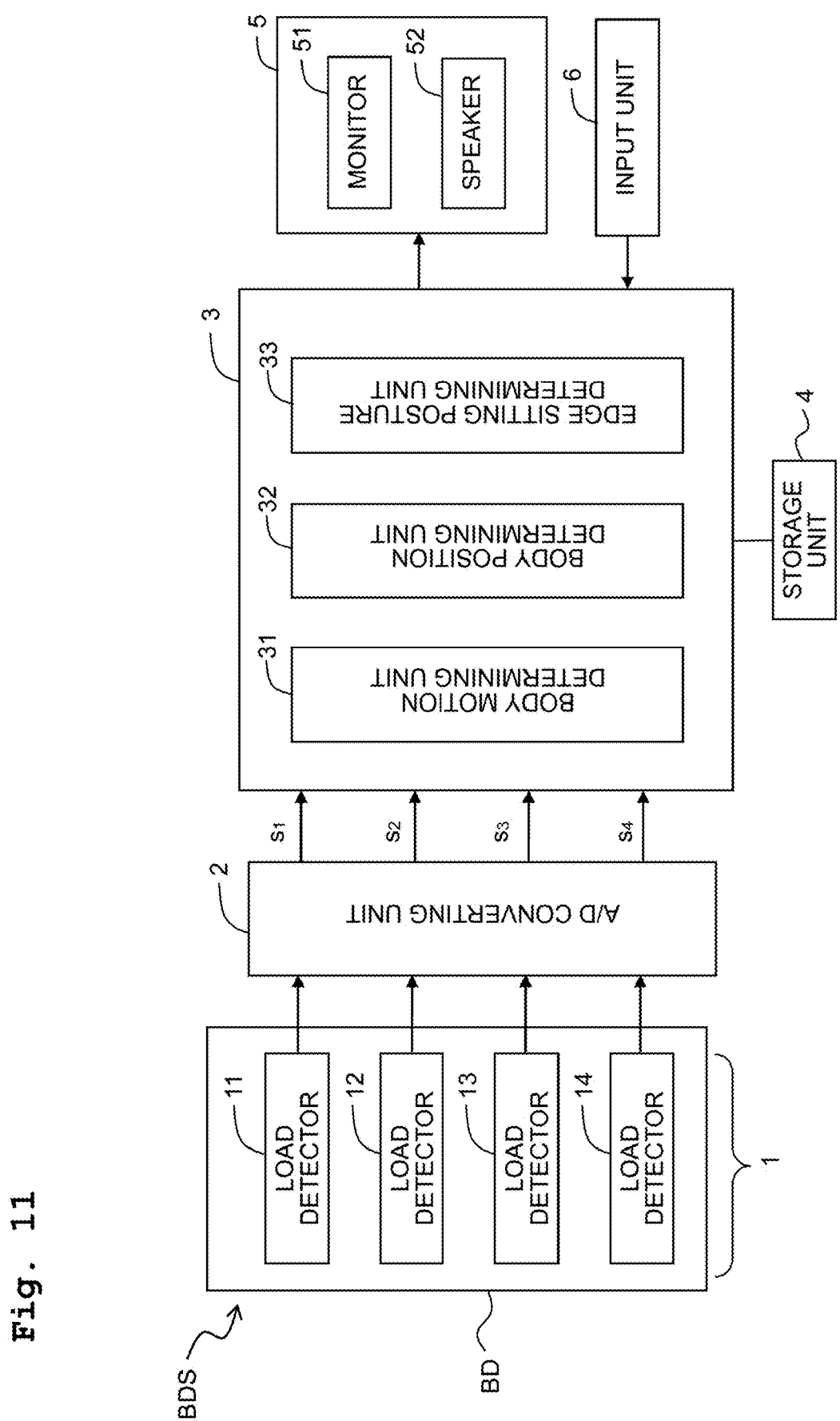
FIG. 11 is a block diagram depicting an overall configuration of a bed system according to a modified embodiment of the present invention.

In the in-bed state monitoring system 100 of the above embodiment, the load detectors 11 to 14 are arranged respectively on the undersides of the casters $C_1$ to $C_4$ attached to the lower ends of the legs $BL_1$ to $BL_4$ of the bed BD. However, there is no limitation thereto. Each of the load detectors 11 to 14 may be provided respectively between one of the four legs of the bed BD and the board of the bed BD. Alternatively, if each of the four legs of the bed BD can be divided into upper and lower portions, each of the load detectors 11 to 14 may be provided between each of the upper legs and each of the lower legs. Further alternatively, the load detectors 11 to 14 may be formed integral with or removable from the bed BD to construct a bed system BDS comprising the bed BD and the in-bed state monitoring system 100 of this embodiment (FIG. 11).

In the in-bed state monitoring system 100 of the above embodiment, between the load detecting unit 1 and the A/D converting unit 2, it is possible to provide a signal amplifying unit to amplify the load signals from the load detecting unit 1, and/or a filtering unit to eliminate the noises from the load signals.

In the in-bed state monitoring system 100 of the above embodiment, the notifying unit 5 may include a simplified visible display means such as a printer for printing out information showing the biological state, a lamp displaying the biological state, and/or the like, instead of the monitor 51 or in addition to the monitor 51. Further, the notifying unit 5 may include a vibration generating unit for carrying out the notification by way of vibration, instead of the speaker 52 or in addition to the speaker 52.

The present invention is not limited to the embodiment described above provided that the feature of the present invention is maintained. Other embodiments, which are conceivable within the scope of the technical concept of the present invention, are also included in the scope of the present invention.

INDUSTRIAL APPLICABILITY

If the in-bed state monitoring system of the present invention is used in hospitals and/or care facilities, then it is possible to prevent accidents such as falls, tumbles and the like from happening when the hospitalized patients and/or care receivers in the care facilities are leaving the bed.

PARTS LIST

1: load detecting unit, 11, 12, 13, 14: load detector, 2: A/D converting unit, 3: control unit, 31: body motion determining unit, 32: body position determining unit, 33: edge sitting posture determining unit, 4: storage unit, 5: notifying unit, 6: input unit, 100: in-bed state monitoring system, BD: bed, BDS: bed system, S: subject.

The invention claimed is:

1. An in-bed state monitoring system for monitoring an in-bed state of a subject on a bed, the system comprising:
   four load detectors which are configured to be placed at four corners of the bed to detect a load of the subject; and
   a controller configured to control the in-bed state monitoring system to:
   compare a first detection value from a first load detector of the four load detectors, and a second detection value from a second load detector of the four detectors so as to predict that the subject is reaching a state of edge sitting posture based on a change in a magnitude relation between the first detection value and the second detection value, the first load detector and the second load detector being placed to interpose the bed between the first and second load detectors in a diagonal direction of the bed.

2. The in-bed state monitoring system according to claim 1, wherein the controller is configured to predict that the subject is reaching the state of edge sitting posture based on a reversal of the magnitude relation between the first and second detection values from the first and second load detectors placed to interpose the bed between the first and second load detectors in the diagonal direction of the bed.

3. The in-bed state monitoring system according to claim 1, wherein the controller is further configured to control the in-bed state monitoring system to:
   determine whether a body motion of the subject is present or not based on a detection value of at least one load detector of the four load detectors; and
   determine a position of the subject in a width direction of the bed based on detection values of two load detectors including at least one load detector, of the four load detectors, which is placed at one side of the bed in the width direction of the bed, and at least one load detector, of the four load detectors, which is placed at other side of the bed in the width direction of the bed, wherein the controller is configured to determine whether the subject is in the state of edge sitting posture or not based on a determination result of the determining whether the body motion of the subject is present or not and a determination result of the determining the position of the subject in the width direction of the bed.

4. The in-bed state monitoring system according to claim 3, wherein the controller is configured to determine whether the subject is in the state of edge sitting posture or not based on the determination result of the determining whether the body motion of the subject is present or not and the determination result of the determining the position of the subject in the width direction of the bed, in a case that the controller has predicted that the subject is reaching the state of the edge sitting posture.

5. The in-bed state monitoring system according to claim 1, further comprising a notifying device configured to carry out a notification based on a determination result of the predicting that the subject is reaching the state of edge sitting posture.

6. A bed system comprising:
a bed; and
the in-bed state monitoring system as defined in claim 1.

7. An in-bed state monitoring system for monitoring an in-bed state of a subject on a bed, the system comprising:
four load detectors which are configured to be placed at four corners of the bed to detect a load of the subject; and
a controller configured to control the in-bed state monitoring system to:

determine whether a body motion of the subject is present or not based on a detection value of at least one load detector of the four load detectors;
determine a position of the subject in a width direction of the bed based on detection values of first and second load detectors, the first load detector being at least one load detector of the four load detectors and being placed at one side of the bed in the width direction of the bed, the second load detector being at least one load detector of the four load detectors and being placed at other side of the bed in the width direction of the bed; and
determine that the subject is in a state of edge sitting posture, based on a determination result of the determining whether the body motion of the subject is present or not and a determination result of the determining the position of the subject in the width direction of the bed, in a case that the body motion of the subject is present and the position of the subject is in a bed edge.

8. The in-bed state monitoring system according to claim 7, further comprising a notifying device configured to carry out a notification in a case that the subject is determined to be in the state of the edge sitting posture.

9. A bed system comprising:
a bed; and
the in-bed state monitoring system as defined in claim 7.

* * * * *